(12) United States Patent
Xie et al.

(10) Patent No.: US 12,708,148 B2
(45) Date of Patent: Aug. 18, 2026

(54) VAPORIZER AND ELECTRONIC VAPORIZATION DEVICE

(71) Applicant: SHENZHEN FIRST UNION TECHNOLOGY CO., LTD., Shenzhen City (CN)

(72) Inventors: Baofeng Xie, Shenzhen City (CN); Zhongli Xu, Shenzhen City (CN); Yonghai Li, Shenzhen City (CN)

(73) Assignee: SHENZHEN FIRST UNION TECHNOLOGY CO., LTD., Shenzhen City (CN)

( * ) Notice: Subject to any disclaimer, the term of this patent is extended or adjusted under 35 U.S.C. 154(b) by 427 days.

(21) Appl. No.: 18/274,708

(22) PCT Filed: Jan. 20, 2022

(86) PCT No.: PCT/CN2022/073030

§ 371 (c)(1),
(2) Date: Jul. 27, 2023

(87) PCT Pub. No.: WO2022/161258

PCT Pub. Date: Aug. 4, 2022

(65) Prior Publication Data

US 2024/0099384 A1 Mar. 28, 2024

(30) Foreign Application Priority Data

Jan. 27, 2021 (CN) ........................ 202110108034.2

(51) Int. Cl.
*A24F 40/485* (2020.01)
*A24F 40/10* (2020.01)
(Continued)

(52) U.S. Cl.
CPC ............ *A24F 40/485* (2020.01); *A24F 40/10* (2020.01); *A24F 40/44* (2020.01); *A24F 40/46* (2020.01); *A61M 15/06* (2013.01)

(58) Field of Classification Search
CPC .............................. A24F 40/10; A24F 40/485
See application file for complete search history.

(56) References Cited

U.S. PATENT DOCUMENTS 10,500,354 B2 * 12/2019 Newberry ............... A24F 40/53
12,364,284 B2 * 7/2025 Zhou ....................... A24F 40/10
(Continued)

FOREIGN PATENT DOCUMENTS

CN 108185536 A 6/2018
CN 210203317 U 3/2020
(Continued)

*Primary Examiner* — Russell E Sparks
(74) *Attorney, Agent, or Firm* — Scully, Scott, Murphy & Presser, P.C.

(57) ABSTRACT

A vaporizer includes a main housing, defining a vapor output channel; a liquid guide element, including a vaporization surface and a liquid absorbing surface; a heating element, arranged on the vaporization surface and configured to heat at least a part of the liquid substrate absorbed by the liquid guide element to generate an aerosol; and a supporting seat, defining a first accommodating space and a second accommodating space separated by a separating plate. The first accommodating space accommodates the liquid guide element, and the supporting seat is in matched connection with the main housing. An air inlet path is formed between the first accommodating space and the second accommodating space, and the air inlet path is configured to guide and convey the air in the second accommodating space to the vicinity of the vaporization surface located in the first accommodating space.

17 Claims, 12 Drawing Sheets

(51) Int. Cl.

| | |
|---|---|
| ***A24F 40/44*** | (2020.01) |
| ***A24F 40/46*** | (2020.01) |
| *A61M 15/06* | (2006.01) |

(56) References Cited

U.S. PATENT DOCUMENTS

| | | | | |
|---|---|---|---|---|
| 12,426,630 | B2 * | 9/2025 | Phillips | A24F 40/42 |
| 2016/0270442 | A1 * | 9/2016 | Liu | A24F 40/485 |
| 2022/0142246 | A1 * | 5/2022 | Liu | A24F 40/40 |
| 2023/0068343 | A1 * | 3/2023 | Batista | A24F 40/30 |

FOREIGN PATENT DOCUMENTS

| | | | |
|---|---|---|---|
| CN | 210929638 | U | 7/2020 |
| CN | 211861815 | U | 11/2020 |
| CN | 211960908 | U | 11/2020 |
| CN | 212117077 | U | 12/2020 |
| CN | 212212684 | U | 12/2020 |
| CN | 214594164 | U | 11/2021 |
| CN | 214629861 | U | 11/2021 |
| CN | 214629863 | U | 11/2021 |
| CN | 214629864 | U | 11/2021 |
| CN | 214962616 | U | 12/2021 |
| CN | 215075498 | U | 12/2021 |
| CN | 215075499 | U | 12/2021 |

* cited by examiner

VAPORIZER AND ELECTRONIC VAPORIZATION DEVICE

This application is a 35 U.S.C. § 371 National Phase conversion of International (PCT) Patent Application No. PCT/CN2022/073030, filed on Jan. 20, 2022, which claims priority to Chinese Patent Application No. 202110108034.2, entitled "Vaporization Core Support Assembly, Vaporizer and Electronic Vaporization Device" and filed with the China National Intellectual Property Administration on Jan. 27, 2021, which is incorporated herein by reference in its entirety. The PCT International Patent Application was filed and published in Chinese.

TECHNICAL FIELD

This application relates to the technical field of electronic vaporization devices, in particular to a vaporizer in an electronic vaporization device. This application further relates to an electronic vaporization device with the vaporizer.

BACKGROUND

An electronic vaporization device is an electronic product for heating and vaporizing liquids such as tobacco tar and liquid medicine into an aerosol for suction.

The electronic vaporization device may include a vaporizer and a power supply component, and the power supply component is configured to supply power to the vaporizer. The vaporizer may include a vaporization core assembly and a vaporization chamber, the vaporization core assembly is configured to generate heat during electrification to vaporize the liquid, and the vaporization chamber is configured to supply the liquid to be heated and vaporized to the vaporization core assembly.

The electronic vaporization device usually uses a porous ceramic body as a capillary liquid guide element for absorbing liquids to absorb a liquid substrate, and heats at least a part of the liquid substrate in the porous ceramic body through a heating element arranged on a vaporization surface of the porous ceramic body to generate an aerosol.

In an existing electronic vaporization device, for example, a vaporization surface of a liquid guide element such as a porous ceramic body is arranged towards an air inlet at the bottom of a vaporizer, so that the air inputted through the air inlet directly impacts the aerosol formed on the vaporization surface. However, particles in the aerosol carried by the air are prone to aggregation, resulting in poor taste.

SUMMARY

This application aims to provide a vaporizer and an electronic vaporization device with the vaporizer to solve the technical problem that a vaporizer in an existing electronic vaporization device directly conveys the air which is not buffered to a vaporization surface.

This application adopts the following technical solution to solve the technical problem: A vaporizer is configured to vaporize a liquid substrate to generate an aerosol. The vaporizer includes: a main housing, defining a vapor output channel located in the main housing; a liquid guide element, including a vaporization surface and a liquid absorbing surface; a heating element, arranged on the vaporization surface and configured to heat at least a part of the liquid substrate absorbed by the liquid guide element to generate an aerosol; and a supporting seat, defining a first accommodating space and a second accommodating space separated by a separating plate. The first accommodating space accommodates the liquid guide element, and the supporting seat is in matched connection with the main housing, so that the vaporization surface of the liquid guide element faces the vapor output channel. An air inlet path is formed between the first accommodating space and the second accommodating space, and the air inlet path is configured to guide and convey the air in the second accommodating space to the vicinity of the vaporization surface located in the first accommodating space.

In a preferred implementation, the supporting seat is provided with an open end, and a side wall of the supporting seat located between the vaporization surface and the open end and the vaporization surface define a vaporization cavity.

In a preferred implementation, the air inlet path is at least partially defined by an air inlet groove on the supporting seat, and the air inlet groove ends at an air inlet higher than the vaporization surface.

In a preferred implementation, the air inlet is provided with an air guide structure, and the air guide structure is configured to guide the air from the air inlet path to the vaporization surface.

In a preferred implementation, the air guide structure includes an inclined plane formed on the supporting seat and inclined relative to the vaporization surface.

In a preferred implementation, the side wall of the supporting seat is provided with a liquid inlet channel, and the liquid inlet channel is in communication with the liquid absorbing surface of the liquid guide element.

In a preferred implementation, the supporting seat is further provided with an air inlet tube, and the air inlet tube is in communication with the second accommodating space through a plurality of through holes.

In a preferred implementation, the plurality of through holes are formed on an end wall of the air inlet tube; and in a depth direction of the second accommodating space, the end wall is higher than the bottommost position of the second accommodating space and lower than the separating plate.

In a preferred implementation, at least one of a bottom surface and a side surface of the second accommodating space is provided with a plurality of leaking liquid storage grooves.

In a preferred implementation, the supporting seat includes a first support and a second support which are in matched connection, the separating plate, the air inlet and the first accommodating space are formed on the first support, and the second accommodating space is formed on the second support.

In a preferred implementation, the second support further includes a blocking wall, and the blocking wall is arranged on one side of the second support; the blocking wall is in matched connection with the first support; and the air inlet path is at least formed between the blocking wall and the first support.

In a preferred implementation, the liquid guide element includes a first wall part where the vaporization surface is located and two second wall parts extending from both sides of the first wall part away from the vaporization surface respectively, and the surface of the first wall part located between the two second wall parts forms at least a part of the liquid absorbing surface.

In a preferred implementation, the vaporizer further includes a first sealing member; and the first sealing member is located between the liquid guide element and a support side wall of the supporting seat to seal and isolate the vaporization surface and the liquid absorbing surface.

In a preferred implementation, the supporting seat is further provided with a conductive element, the conductive element abuts against the heating element to conduct electricity, and at least partially extends or is exposed outside the supporting seat to form a first electrical contact for supplying power to the heating element.

In a preferred implementation, the vaporizer further includes a second sealing member, and the second sealing member has a skirted part arranged in a circumferential direction and is provided with a liquid guide hole and a plug-in hole; and the second sealing member sleeves the supporting seat, and the supporting seat is at least partially inserted into the main housing, so that the skirted part of the second sealing member is clamped between the supporting seat and the main housing to form a seal, and a first end of the vapor output channel is inserted in the plug-in hole.

In a preferred implementation, the second sealing member is provided with a ventilation groove, and the ventilation groove is in communication with the atmosphere and the liquid accommodating space, so as to convey the air into the liquid accommodating space under the action of a pressure difference; or the second sealing member is provided with a non-return valve, and the non-return valve is configured to be opened under the action of a pressure difference to convey the air into the liquid accommodating space.

In a preferred implementation, the supporting seat defines that a side wall of the first accommodating space is provided with a step part, and the step part supports the part of the second sealing member inserted into the first accommodating space.

This application further adopts the following technical solution to solve the technical problem: An electronic vaporization device includes a vaporizer configured to vaporize a liquid substrate to generate an aerosol, and a power supply assembly configured to supply power to the vaporizer, where the vaporizer includes any one of the vaporizers as described above.

This application has the following beneficial effects: In the vaporizer of this embodiment, since the supporting seat defines the first accommodating space and the second accommodating space separated by the separating plate and the first accommodating space accommodates the liquid guide element, the vaporization surface of the liquid guide element faces away from the second accommodating space. As a result, the external air first flows through the second accommodating space, is buffered in the second accommodating space, and is then conveyed to the vaporization surface through the air inlet groove in communication with the first accommodating space and the second accommodating space. The buffered air is not easy to cause the aggregation of particles in the aerosol, and can maintain the taste of the aerosol. In addition, by arranging the air inlet of the air inlet groove to be higher than the vaporization surface of the liquid guide element accommodated in the first accommodating space, the liquid can be prevented from leaking from the vaporization surface into the air inlet groove through the air inlet, thereby also achieving an anti-leakage effect. Correspondingly, the electronic vaporization device with the foregoing vaporizer also has air-buffering and anti-leakage effects.

BRIEF DESCRIPTION OF THE DRAWINGS

One or more embodiments are exemplarily described with reference to the corresponding accompanying drawings, and the exemplary descriptions are not to be construed as limiting the embodiments. Elements in the accompanying drawings that have same reference numerals are represented as similar elements, and unless otherwise particularly stated, the figures in the accompanying drawings are not drawn to scale.

DETAILED DESCRIPTION

For ease of understanding of this application, this application is described below in more detail with reference to the accompanying drawings and specific embodiments. It should be noted that, when an element is expressed as "being fixed to" another element, the element may be directly on the another element, or one or more intermediate elements may exist between the element and the another element. When an element is expressed as "being connected to" another element, the element may be directly connected to the another element, or one or more intermediate elements may exist between the element and the another element. The terms “vertical”, “horizontal”, “left”, “right”, “inside”, “outside”, and similar expressions used in this specification are merely used for an illustrative purpose.

Unless otherwise defined, the meanings of all technical and scientific terms used in this specification are the same as the meanings usually understood by a person skilled in the technical field to which this application belongs. The terms used in the specification of this application are merely intended to describe specific embodiments, but are not intended to limit this application. The term “and/or” used in this specification includes any or all combinations of one or more related listed items.

In addition, technical features involved in different embodiments of this application described below may be combined together if there is no conflict.

Figure 1:
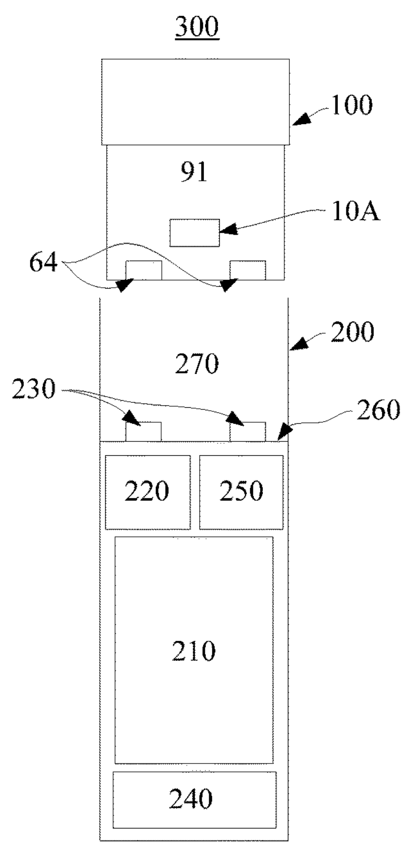
FIG. 1 is a planar schematic view of an electronic vaporization device provided in an embodiment of this application.

An embodiment of this application provides an electronic vaporization device 300. Referring to FIG. 1, a structure of the electronic vaporization device 300 includes: a vaporizer 100 configured to store a liquid substrate and vaporize the liquid substrate to generate an aerosol; and a power supply assembly 200 configured to supply power to the vaporizer 100. The liquid substrate may be a liquid, such as tobacco tar, liquid medicine, or the like. In this specification, the liquid substrate may also be referred to as a liquid, evaporation may also be referred to as vaporization, and the aerosol may also be referred to as vapor, mist or vaporized gas.

In an optional embodiment, for example, as shown in FIG. 1, the power supply assembly 200 includes a receiving cavity 270, arranged on an end along a longitudinal direction and configured to receive and accommodate at least a part of the vaporizer 100, and a first electrical contact 230, at least partially exposed to an inner surface of the bottom of the receiving cavity 270 and configured to be electrically connected to the vaporizer 100 to supply power to the vaporizer 100 when at least a part of the vaporizer 100 is received and accommodated in the power supply assembly 200.

According to the preferred embodiment shown in FIG. 1, a second electrical contact 64 is arranged on an end of the vaporizer 100 opposite to the power supply assembly 200 along a longitudinal direction, so that when the at least a part of the vaporizer 100 is received in the receiving cavity 270, the second electrical contact 64 become conductive through being in contact with and abutting the first electrical contact 230.

A sealing member 260 may be arranged in the power supply assembly 200, and at least a part of an internal space of the power supply assembly 200 is separated by the sealing member 260 to form the receiving cavity 270. In the preferred embodiment shown in FIG. 1, the sealing member 260 is configured to extend along a cross section direction of the power supply assembly 200 and is prepared from a flexible material, so as to prevent the liquid substrate seeping from the vaporizer 100 to the receiving cavity 270 from flowing to components such as a controller 220 and a sensor 250 inside the power supply assembly 200.

In the preferred embodiment shown in FIG. 1, the power supply assembly 200 may further include a battery cell 210 close to another end opposite to the receiving cavity 270 along the longitudinal direction for supplying power; and a controller 220 arranged between the battery cell 210 and an accommodating cavity and operable to guide a current between the battery cell 210 and the first electrical contacts 230.

The power supply assembly 200 may further include a sensor 250 configured to sense the suction air generated by the vaporizer 100 during suction, so that the controller 220 controls the battery cell 210 to output a current to the vaporizer 100 based on a detection signal of the sensor 250.

Further, in the preferred embodiment shown in FIG. 1, a charging interface 240 is arranged on another end of the power supply assembly 200 facing away from the receiving cavity 270, and is configured to charge the battery cell 210 through a connection with an external charging device.

Further, in the embodiment shown in FIG. 1, the vaporizer 100 may mainly include: a liquid accommodating space 91, configured to store a liquid substrate; and a vaporization core assembly 10A, configured to absorb the liquid substrate from the liquid accommodating space 91 by capillary infiltration, and heat and vaporize the liquid substrate to generate an aerosol for suction.

Figure 2:
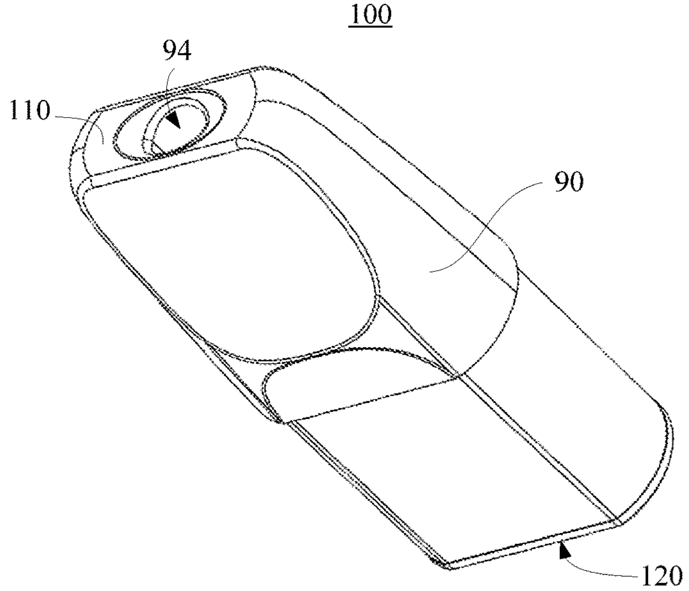
FIG. 2 is a three-dimensional schematic assembly view of a vaporizer of the electronic vaporization device shown in FIG. 1.
Figure 3:
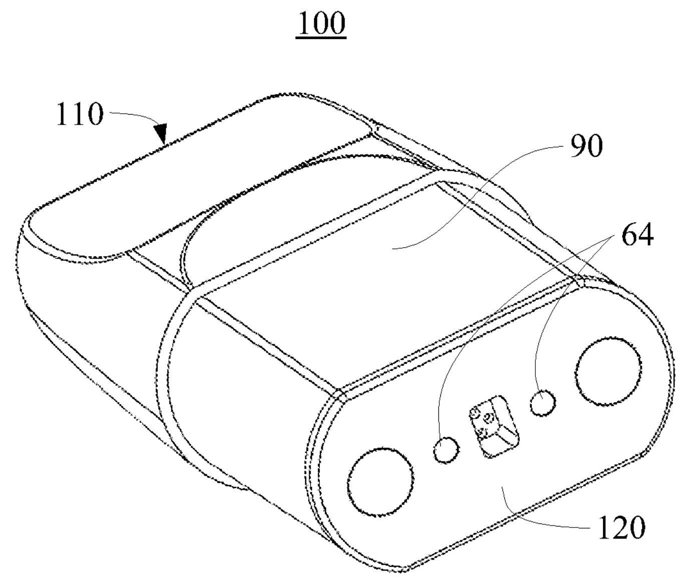
FIG. 3 is another three-dimensional schematic assembly view of the vaporizer shown in FIG. 2.
Figure 4:
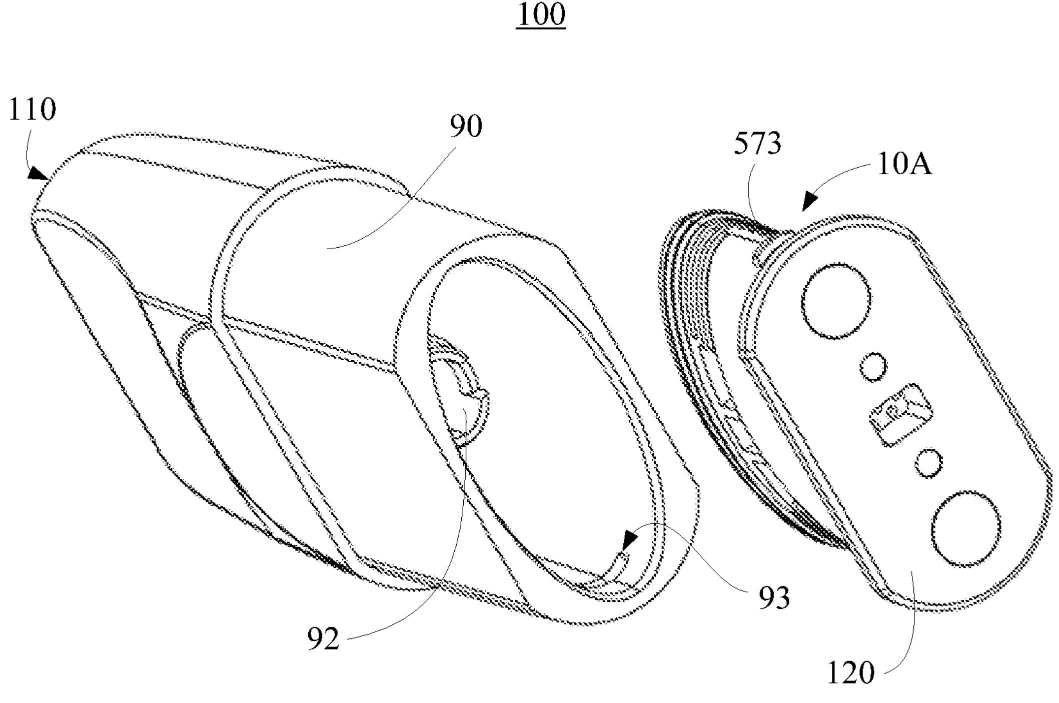
FIG. 4 is a three-dimensional schematic exploded view of the vaporizer shown in FIG. 2.

Further, FIG. 2 to FIG. 4 show a structure of a preferred embodiment of the vaporizer 100 in FIG. 1. As shown in the figures, the vaporizer 100 has a near end 110 and a far end 120 facing away from each other in a longitudinal direction. In use, the near end 110 is used as an end for a user to inhale, and the far end 120 is used as an end received in the receiving cavity 270. A specific external structure of the vaporizer 100 includes a main housing 90, and the main housing 90 is roughly constructed into a hollow cylinder, and is provided with a suction port 94 located on the near end 110, and an opening located on the far end 120, and thus it is convenient to assemble functional components inside the main housing 90 through the opening.

In some embodiments, as shown in FIG. 4 to FIG. 7, the vaporizer 100 may include the main housing 90 and a vaporization core assembly 10A. The vaporization core assembly 10A is in matched connection with the main housing 90 through a buckle 573 and a slot 93. The buckles 573 may be arranged on two opposite outer sides of the vaporization core assembly 10A, and the slots 93 may be arranged on two opposite inner sides of the main housing 90, so that during assembly, each buckle 573 may be clamped in each corresponding slot 93 to achieve the installation and connection of the vaporization core assembly 10A and the main housing 90. Alternatively, the vaporization core assembly 10A and the main housing 90 may be connected through a binder or may also be connected in a detachable connection manner.

The main housing 90 defines a liquid accommodating space 91 and is provided with a vapor output channel 92 located in the main housing 90. For example, the liquid accommodating space 91 may be enclosed by an inner surface of the main housing 90, an outer surface of the vapor output channel 92, and an upper surface of the vaporization core assembly 10A. Since the main housing 90 defines the liquid accommodating space 91, the main housing 90 may also be referred to as a vaporization chamber, a tar chamber, or the like. The vapor output channel 92 may be a vapor output tube.

The vapor output channel 92 may be formed at the center of the main housing 90 and extends along a longitudinal direction, and the vapor output channel and the main housing 90 may be integrally prepared by a mold. A second end 923 serving as an upper end of the vapor output channel 92 forms a suction port 94, so that the aerosol generated inside the vaporizer 100 is outputted to the suction port 94. A tail end of a first end 921 serving as a lower end of the vapor output channel 92 may be provided with a notch 922, and the notch 922 is formed on a tube wall of the vapor output channel 92 and may have a square projection contour. Two notches 922 may be provided and may be arranged oppositely. The second end 923 of the vapor output channel 92 opposite to the first end 921 forms the suction port 94. The vapor output channel 92 may be provided with a stop part 924 at a position adjacent to the first end 921. The stop part 924 may be an annular step surface, which may be a transition surface between a section with a larger diameter and the first end 921 with a smaller diameter of the vapor output channel 92. The section with a larger diameter may extend to the second end 923. The stop part 924 is configured to be in stop fit with an upper surface of a second sealing member 70 (referring to FIG. 8) to define a depth of the vapor output channel 92 inserted into the second sealing member 70.

Figure 7:
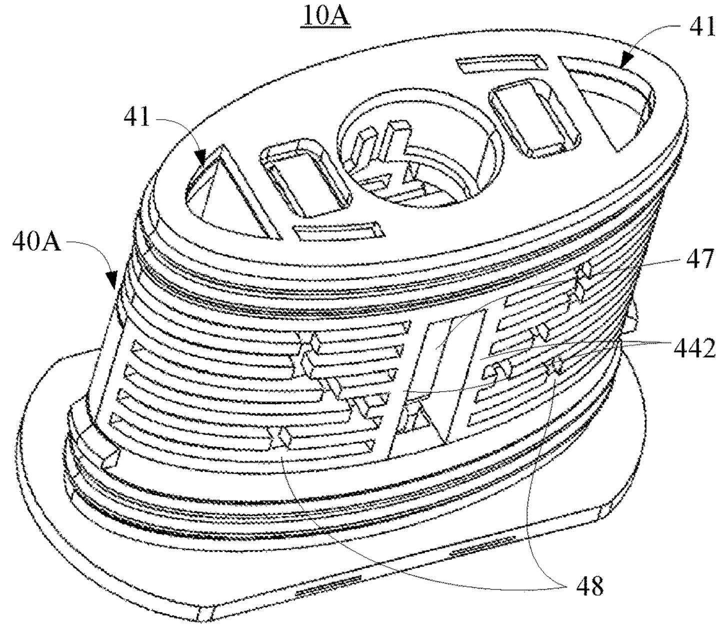
FIG. 7 is a three-dimensional schematic view of a vaporization core assembly of the vaporizer shown in FIG. 2.
Figure 8:
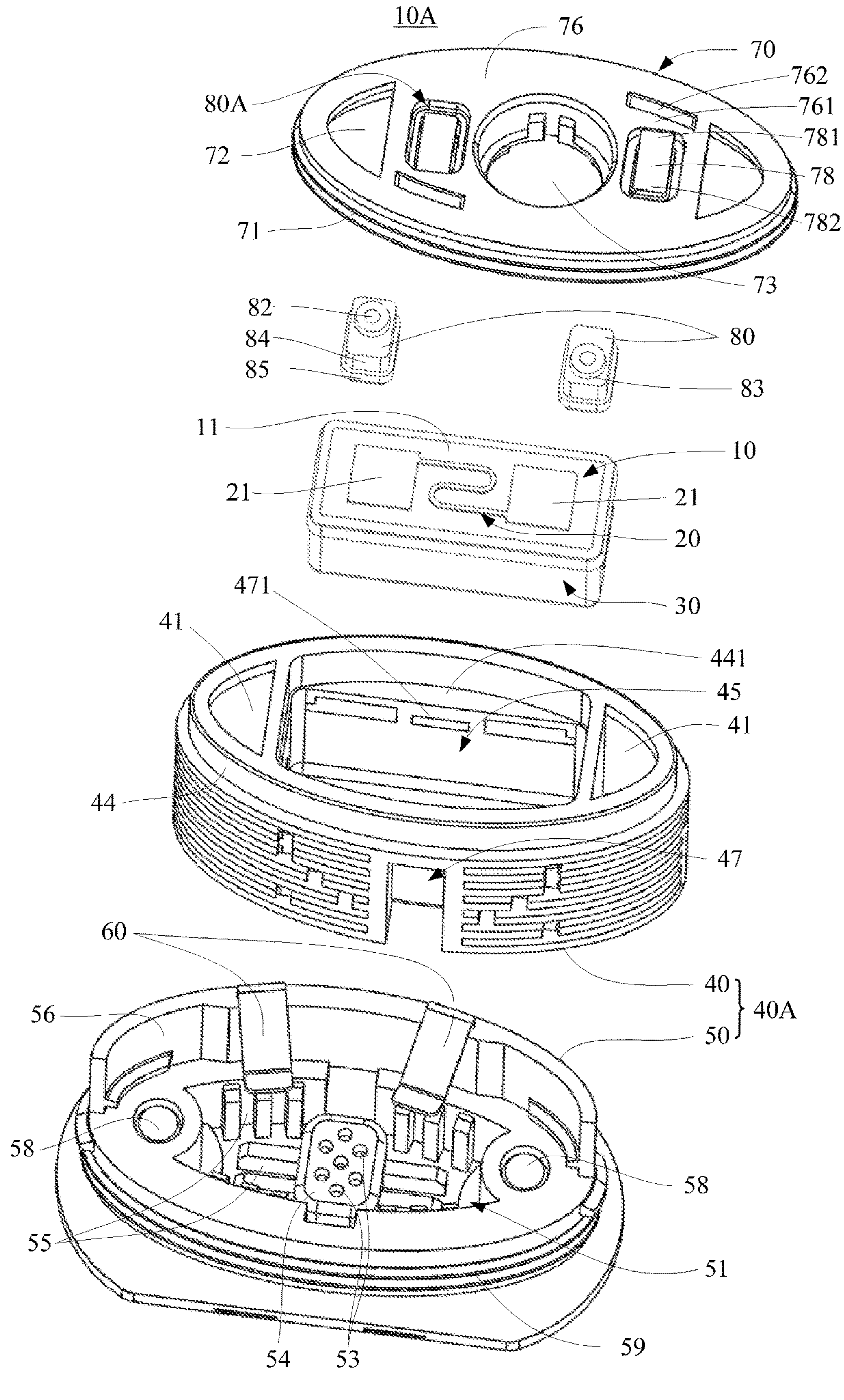
FIG. 8 is a three-dimensional schematic exploded view of the vaporization core assembly shown in FIG. 7.
Figure 9:
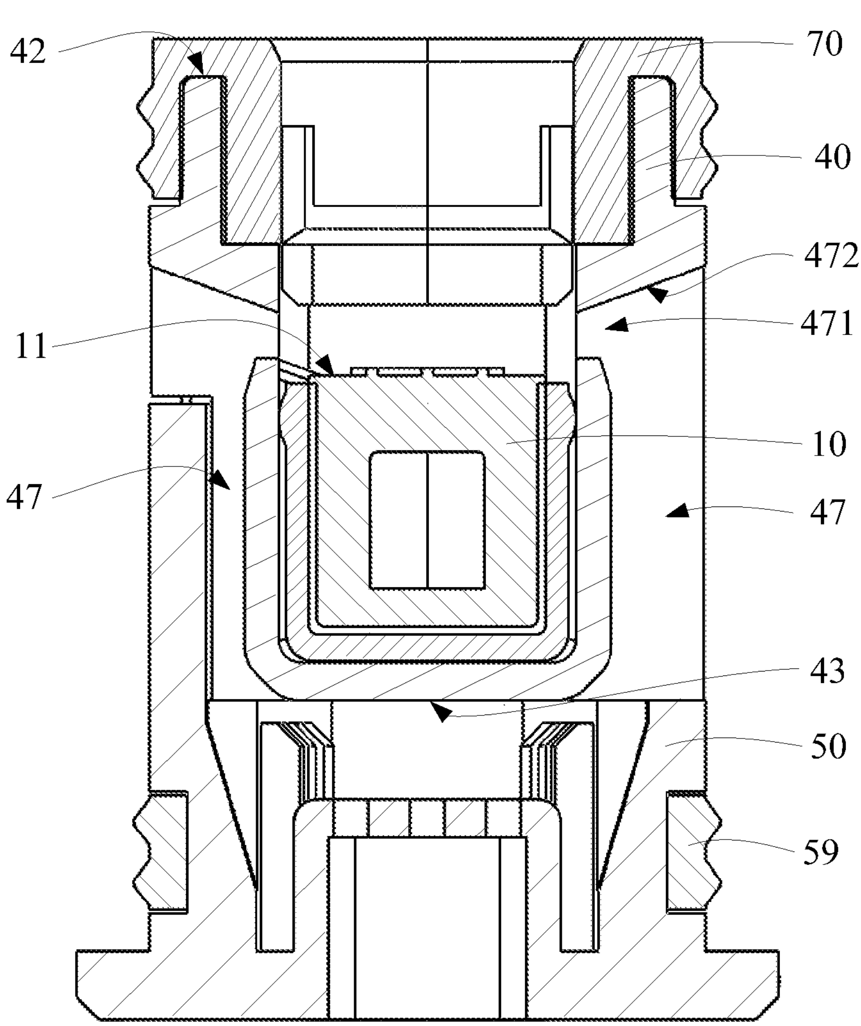
FIG. 9 is a schematic cross-sectional view of the vaporization core assembly shown in FIG. 7.

As shown in FIG. 7 to FIG. 9, the vaporization core assembly 10A may include a liquid guide element 10, a heating element 20, a first sealing member 30, a supporting seat 40A, and the like. The supporting seat 40A may be of a rigid structure for accommodating and supporting the liquid guide element 10, the heating element 20 and the first sealing member 30, so that the vaporization core formed by the liquid guide element 10 and the heating element 20 is stably maintained in the main housing 90. Since the supporting seat 40A is mainly configured to support the vaporization core, the supporting seat 40A may also be referred to as a vaporization core support assembly.

Figure 10:
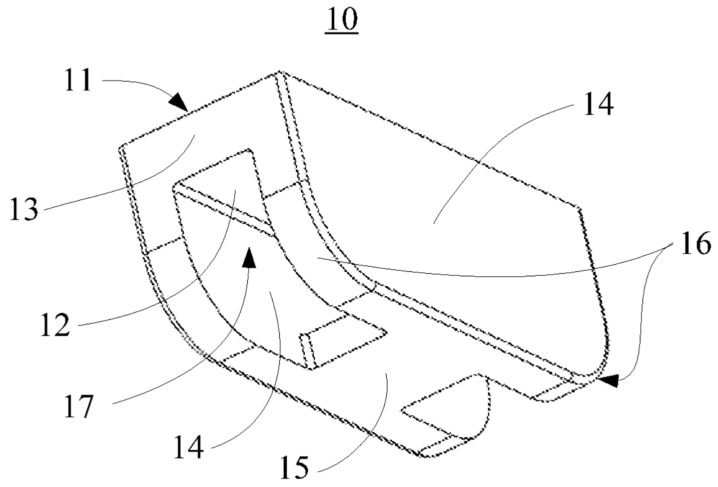
FIG. 10 is a three-dimensional schematic view of a liquid guide element of the vaporization core assembly shown in FIG. 8.

With reference to FIG. 10, the liquid guide element 10 may include a vaporization surface 11 and a liquid absorbing surface 12 facing away from the vaporization surface 11. The liquid guide element 10 may be prepared from a material having capillary channels or pores, for example, a hard or rigid capillary structure such as fiber cotton, a porous ceramic body, a fiberglass rope, porous glass ceramic, or porous glass. The liquid guide element 10 is in fluid communication with the liquid accommodating space 91 to absorb the liquid substrate conveyed from the liquid accommodating space 91. The vaporization surface 11 of the liquid guide element 10 may be an upper surface facing the vapor output channel 92, and the upper surface is preferably a plane extending along a cross section of the main housing 90.

The heating element 20 is arranged on the vaporization surface 11, and is configured to, for example, heat at least a part of the liquid substrate absorbed by the liquid guide element 10 during electrification to generate an aerosol and release the aerosol escaped from the vaporization surface 11 into the vapor output channel 92. For example, the heating element 20 may be formed on the vaporization surface 11 of the liquid guide element 10 in a manner of mounting, printing, deposition, or the like. In some embodiments, the heating element 20 may be made of a material such as stainless steel, nickel chromium alloy, iron chromium aluminum alloy, or metal titanium. As shown in FIG. 8, the heating element 20 is a conductive trajectory in a winding or circuitous pattern, and may include conductive terminals 21 on both ends. The conductive terminal 21 may be in the form of a gasket, which may be square, circular, elliptical, or the like.

Figure 11:
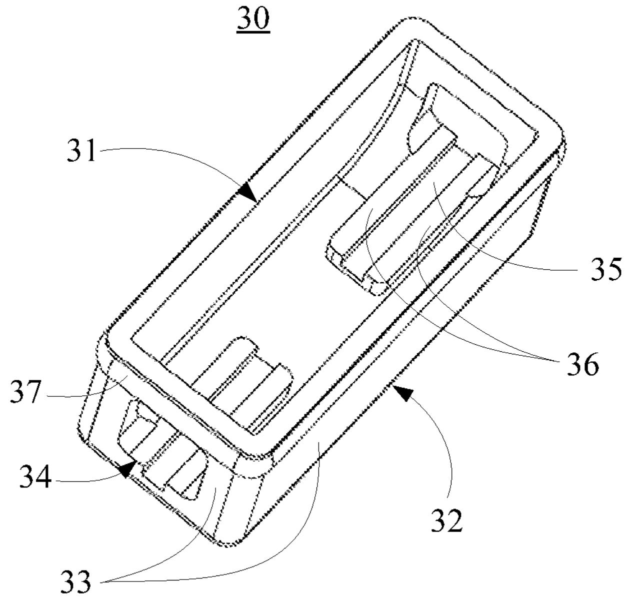
FIG. 11 is a three-dimensional schematic view of a first sealing member of the vaporization core assembly shown in FIG. 8.

With reference to FIG. 11, the first sealing member 30 may be located between the liquid guide element 10 and the support side wall 44 of the supporting seat 40A to seal and isolate the vaporization surface 11 and the liquid absorbing surface 12. That is, the liquid provided by the liquid accommodating space 91 may only enter the liquid guide element 10 through the liquid absorbing surface 12 and is then conveyed to the vaporization surface 11. The first sealing member 30 may be roughly cup-shaped, so that the liquid guide element 10 may be accommodated in a recess of the cup-shaped first sealing member 30. The first sealing member 30 may be provided with a first open end 31, a first closed end 32 opposite to the first open end 31, and a sealing member side wall 33 extending from the first closed end 32 to the first open end 31. Multiple sealing member side walls 33 may be provided. For example, a first sealing member 30 in a roughly cubic shape may include four sealing member side walls 33. The first sealing member 30 is enclosed by the sealing member side wall 33 and the first closed end 32 to form an accommodating space for accommodating the liquid guide element 10 and exposing the vaporization surface 11. For example, the vaporization surface 11 may be roughly flush with the first open end 31 so as to be exposed towards the outside of the first sealing member 30. The first sealing member 30 is further provided with a liquid inlet 34 on the sealing member side wall 33, so that the liquid absorbing surface 12 is in communication with the outside through the liquid inlet 34 and is then communicated to the liquid accommodating space 91 during assembly. In some embodiments, the liquid guide element 10 may be roughly in a flat shape and is supported in the first sealing member 30 through a supporting structure, so that the liquid absorbing surface 12 of the liquid guide element 10 is in communication with the outside through the liquid inlet 34. The first sealing member 30 may be made of a silicone sealant material.

With reference to FIG. 10 and FIG. 11, after the liquid guide element 10 is placed in the first sealing member 30, the other five surfaces of the liquid guide element 10, except for the vaporization surface 11, may be enveloped by the first sealing member 30 to prevent the liquid absorbed by the liquid guide element 10 from leaking from these surfaces, so that the anti-leakage effect is better. It is noted that although the sealing member side walls 33 of the first sealing member 30 are provided with the liquid inlet 34, the parts of these sealing member side walls 33, except for the liquid inlets 34, may still play a sealing role to achieve the anti-leakage effect.

Further, two liquid inlets 34 may be provided. For example, two opposite sealing member side walls 33 of the first sealing member 30 are respectively provided with one liquid inlet 34. This can promote a constant supply of the liquid to the liquid guide element 10.

In addition, the sealing member side wall 33 of the first sealing member 30 without the liquid inlet 34 completely covers the corresponding side surface of the liquid guide element 10. This can achieve sealing for gases and liquids, such as avoiding leakage of liquids from these corresponding side surfaces to the outside, absorption of external water vapor, and the like. The first sealing member 30 may be in a cuboid shape, so the two liquid inlets 34 may be formed in two opposite sealing member side walls 33 in a length direction of the first sealing member 30. Correspondingly, two opposite sealing member side walls 33 in a width direction of the first sealing member 30 remain intact without holes.

In some embodiments, with reference to FIG. 11, the sealing member side walls 33 of the first sealing member 30 may be provided with a closed annular convex rib 37 surrounding the first sealing member 30 along a circumferential direction. When the first sealing member 30 accommodating the liquid guide element 10 is assembled with the supporting seat 40A, the convex rib 37 can closely abut against an inner wall of the supporting seat 40A, thereby stably sealing a gap between the first sealing member 30 and the supporting seat 40A to prevent liquid leakage.

In some embodiments, with reference to FIG. 11, the first open end 31 of the first sealing member 30 may be located in a plane, for example, aligned with the vaporization surface 11. Correspondingly, the convex rib 37 may be arranged adjacent to the first open end 31. Alternatively, the first open end 31 of the first sealing member 30 may be provided with a concave end surface. For example, top ends of the two opposite sealing member side walls 33 in the width direction of the first sealing member 30 are respectively provided with a concave notch, which may easily expose parts of the two side surfaces of the liquid guide element 10 accommodated in the first sealing member 30, thereby facilitating the extraction of the liquid guide element 10 from the first sealing member 30. Similarly, the convex rib 37 may be arranged adjacent to the first open end 31 with a concave end surface, so that the convex rib 37 is no longer located in the same plane.

Figure 5:
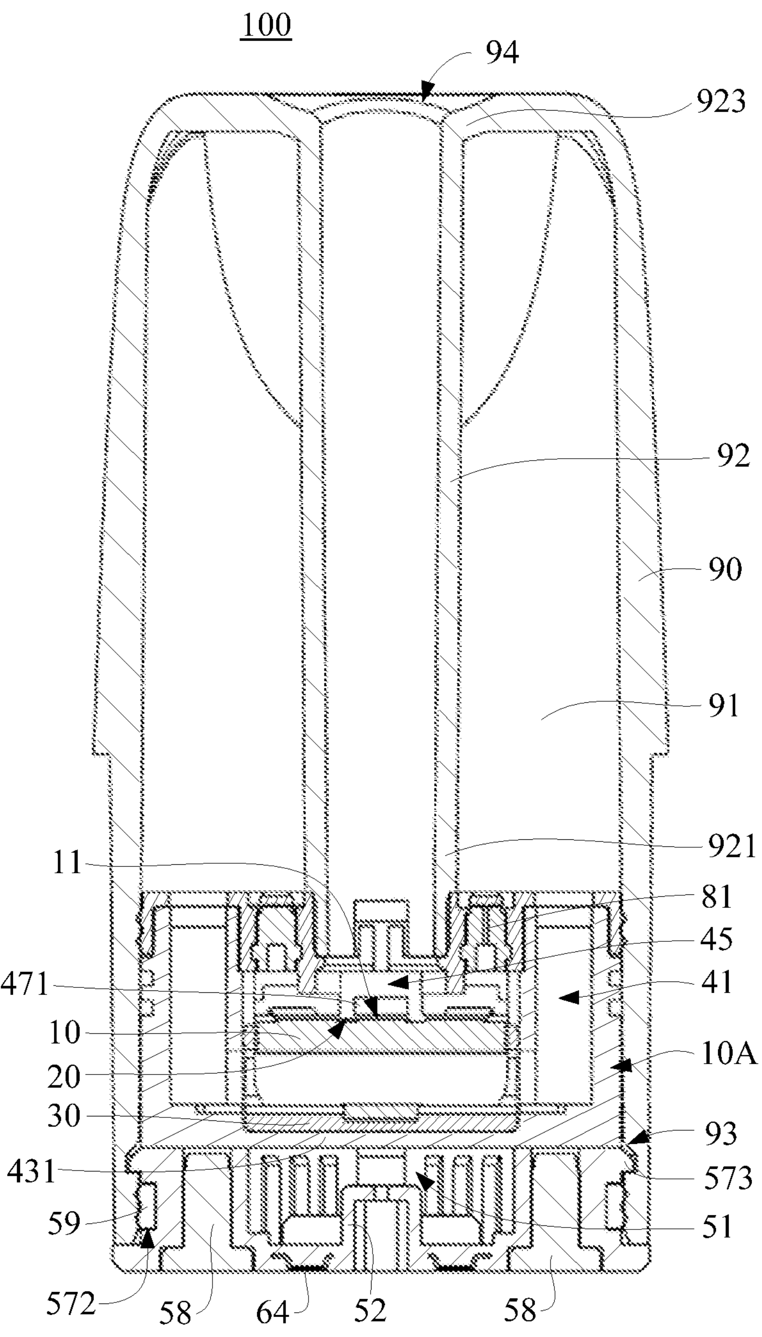
FIG. 5 is a schematic cross-sectional view of the vaporizer shown in FIG. 2.
Figure 6:
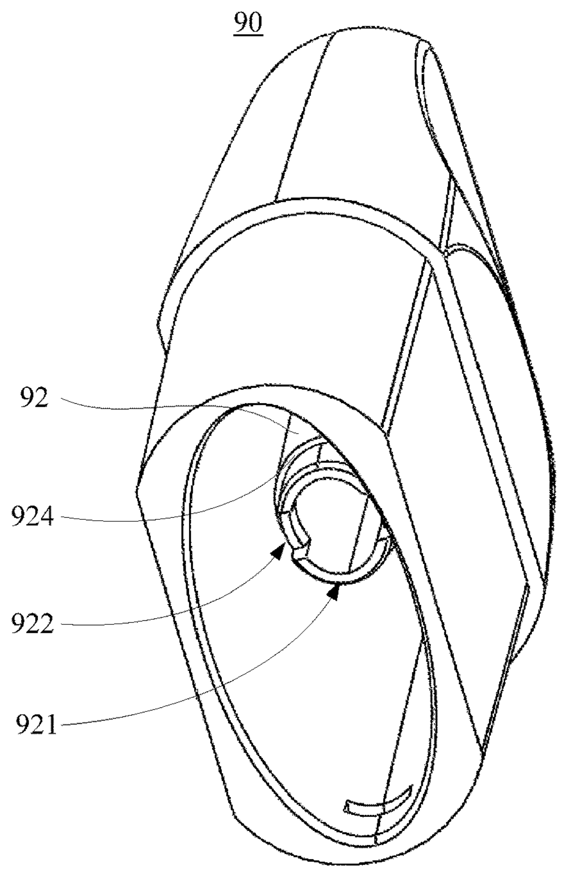
FIG. 6 is a three-dimensional schematic view of a main housing of the vaporizer shown in FIG. 2.

With reference to FIG. 5, the supporting seat 40A may accommodate the liquid guide element 10, the heating element 20 and the first sealing member 30; and the supporting seat 40A is in matched connection with the main housing 90, so that the vaporization surface 11 of the liquid guide element 10 faces the vapor output channel 92.

When the vaporization surface 11 of the liquid guide element 10 is arranged to face the vapor output channel 92, since the vaporization surface 11 is arranged opposite to the power supply assembly 200 and facing the suction port 94, the heating element 20 on the vaporization surface 11 generates heat, the liquid on the vaporization surface 11 absorbs the heat and is vaporized, and the generated vapor does not need to pass through the liquid guide element 10, but directly enters a suction channel of the vapor output channel 92 and reaches the suction port 94 to be sucked by the user, so as to reduce the loss generated by the vapor passing through the vaporization core, ensure that sufficient vapor is effectively absorbed by the user in a unit time, and further increase the effective vapor generated by the electronic vaporization device 300 in a unit time. Moreover, a distance between the vaporization surface 11 and the suction port 94 is relatively small, so a path of the vapor flowing to the suction port 94 is the shortest, which can also reduce the loss of the vapor in the suction channel to further ensure the effective vapor generated by the electronic vaporization device 300 in a unit time.

In some embodiments, with reference to FIG. 10, the liquid guide element 10 may include a first wall part 13 where the vaporization surface 11 is located and two second wall parts 14 extending from both sides of the first wall part 13 away from the vaporization surface 11 respectively, and the surface of the first wall part 13 between the two second wall parts 14 forms at least a part of the liquid absorbing surface 12. The two second wall parts 14 may be of supporting structures simply, or structures with the same material as the liquid guide element 10, so that the liquid guide element 10 may be supported in the first sealing member 30, and a liquid guide effect may be achieved. In other words, opposite inner surfaces of the two second wall parts 14 may also serve as a part of the liquid absorbing surface 12. It is easy to understand that a liquid channel 17 which extends horizontally is defined between the two second wall parts 14. After assembly, the liquid channel 17 extends from one of the liquid inlets 34 of the first sealing member 30 to the other liquid inlet 34 and is in communication with the liquid inlet 34. During use, the liquid substrate flowing from liquid inlet channel 41 formed in the side wall of the supporting seat 40A enters the liquid channel 17 and is then absorbed by capillary channels in the liquid guide element 10.

Further, with reference to FIG. 10, the two second wall parts 14 may be connected at tail ends away from the first wall part 13 through a connecting wall 15. By using the connecting wall 15, the structural strength of the entire liquid guide element 10 can be enhanced. Moreover, when the connecting wall 15 and the two second wall parts 14 are made of the same porous material as the first wall part 13, the connecting wall 15 may also play a liquid guide role, which can absorb the liquid and convey the liquid to the first wall part 13 through the second wall parts 14. In addition, as shown in FIG. 10, the connecting wall 15 may only be connected to parts of the tail ends of the two second wall parts 14. For example, a length of the connecting wall 15 may be about ⅓ of a length of the first wall part 13. Alternatively, the connecting wall 15 may be connected to the entire tail ends of the two second wall parts 14. For example, the connecting wall 15 may extend in a length direction, and may be connected to the entire tail ends of the two second wall parts 14 located in an extension direction of the connecting wall 15. It is easy to understand that a through hole extending along a length direction of the liquid guide element 10 may be arranged below the vaporization surface 11 of the liquid guide element, so that a wall surface of the through hole is used as the liquid absorbing surface 12. In addition, the through hole may be a hole penetrating along the length direction of the liquid guide element 10, or a blind hole that starts from both ends of the liquid guide element 10 and ends in a middle position of the liquid guide element 10.

Further, with reference to FIG. 10, the connecting wall 15 may be arranged parallel to the first wall part 13. In addition, both sides of each second wall part 14 may transition to the tail end of the second wall part 14 through an arc surface 16. In other words, chamfer shapes may be set on both sides of each second wall part 14, which facilitates the assembly of the liquid guide element 10 into the first sealing member 30.

In some embodiments, with reference to FIG. 11, the first sealing member 30 may be provided with a guide groove 35 extending from the liquid inlet 34 into the first sealing member 30. By arranging the guide groove 35, it is beneficial to guide the liquid in the liquid accommodating space 91 into the first sealing member 30 by capillary action, so as to avoid the liquid from staying at the liquid inlets 34. More specifically, since the liquid guide element 10 has gas exchange performance, external gas may enter the liquid channel 17 under the action of gas pressure difference and flow to the liquid accommodating space 91 through the liquid inlet 34, and then, the external gas will encounter with the liquid inputted through the liquid accommodating space 91 at the liquid inlet 34, which causes the liquid to stay at the liquid inlets 34. The guide groove 35 can avoid the staying. Further, the guide groove 35 may be defined by two strip bodies 36 protruding upwards from the first closed end 32 of the first sealing member 30. The two strip bodies 36 may extend to abut against the connecting wall 15 of the liquid guide element 10 assembled in the first sealing member 30. In addition, three or more strip bodies 36 may be provided, and every two adjacent strip bodies 36 define one guide groove.

In some embodiments, with reference to FIG. 5 and FIG. 8, the side wall of the supporting seat 40A may be provided with liquid inlet channels 41, and the liquid inlet channels 41 are respectively in communication with the liquid accommodating space 91 and the liquid absorbing surface 12 of the liquid guide element 10. The liquid inlet channel 41 may include a first part which extends along a longitudinal direction and is in communication with the liquid accommodating space 91, and a second part which is in communication with the liquid guide element 10. The second part may be horizontal or oblique downwards from the first part to the liquid guide element 10, and the obliquely arranged second part is more beneficial to guide the liquid substrate to flow to the liquid guide element 10. In addition, two liquid inlet channels 41 may be provided and may be respectively arranged on both sides of the supporting seat 40A. It is noted that the cross section of the supporting seat 40A may be square, circular, elliptical, or the like. Moreover, even if the cross section of the supporting seat 40A is circular or elliptical, four side parts may still be divided. For example, for the elliptical supporting seat 40A shown in FIG. 8, two sides in a length direction may be considered as two opposite sides, two sides in a width direction may be considered as the other two opposite sides, and the two liquid inlet channels 41 are respectively arranged in the two opposite sides in the length direction.

In the foregoing embodiment, by arranging the liquid inlet channel 41, the liquid such as tobacco liquid may enter the liquid guide element 10 through the liquid inlet channel 41 and is guided upwards to the vaporization surface 11 of the liquid guide element 10 for vaporization through capillary action, the vaporization volume of tobacco tar is completely supplied through capillary action, and the liquid will not leak downwards during the intermediate process, so the anti-leakage effect is better.

Figure 16:
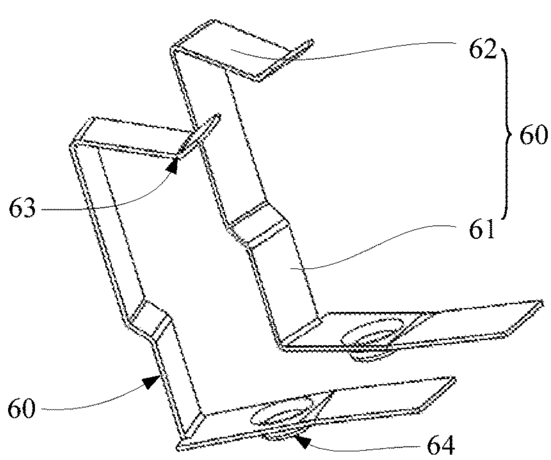
FIG. 16 is a three-dimensional schematic view of a conductive element of the vaporization core assembly shown in FIG. 8.

In some embodiments, with reference to FIG. 8 and FIG. 16, the supporting seat 40A may be provided with a conductive element 60. Two conductive elements 60 may be provided. Each conductive element 60 may include a first part 61 at least partially extending in the supporting seat 40A and a second part 62 bent relative to the first part 61 towards the heating element 20 on the liquid guide element 10 in the supporting seat 40A. The second part 62 may be configured to be in abutting contact with the conductive terminal 21 of the heating element 20 to achieve conductive connection. At least the second part 62 of the conductive element 60 extends or is exposed outside the supporting seat 40A, and an electrical contact 63 for supplying power to the heating element 20 is formed. The first part 61 of the conductive element 60 may further include a second electrical contact 64. The part in a vertical direction of the first part 61 and the second part 62 may have a same width, and the part in a horizontal direction of the first part 61 (that is, the part provided with the second electrical contact 64) may have a slightly larger width.

At least a part of the first part 61 of the conductive element 60 may be molded in the supporting seat 40A, and the second electrical contact 64 is exposed from the bottom of the supporting seat 40A, thereby facilitating the conductive connection with the power supply assembly 200. For example, the conductive element 60 is at least partially buried or embedded into the supporting seat 40A. The conductive element 60 and the supporting seat 40A may be integrally prepared through moldable methods such as in-mold injection molding or hot press molding. In addition, the conductive element 60 may be formed by bending a sheet metal substrate.

In some embodiments, the conductive element 60 may be made of low-resistivity and high-conductivity metal or alloy materials such as gold, silver and copper to guide a current between the power supply assembly 200 and the heating element 20 during use, thereby supplying power to the heating element 20. At least a part of the lower end of the conductive element 60 may be formed into the second electrical contact 64 through stamping deformation, and at least a part of an upper end of the conductive element 60 may be in a bent shape to form an elastic first electrical contact 63 which is conductively connected to the heating element 20, thereby ensuring stable conductive contact with the heating element 20. The surface of the second electrical contact 64 may be flush with the surface of the far end 120 forming the vaporizer 100. The elastic first electrical contact 63 may include a bent V shape or U shape in the figure.

In some embodiments, with reference to FIG. 5 and FIG. 8, the supporting seat 40A may define a first accommodating space 45 and a second accommodating space 51 which are separated by a separating plate 431. An air inlet path is formed between the first accommodating space 45 and the second accommodating space 51, and the air inlet path is configured to guide and convey the air in the second accommodating space 51 to the vicinity of the vaporization surface 11 located in the first accommodating space 45. During assembly, the first accommodating space 45 accommodates the liquid guide element 10, causing the vaporization surface 11 to face away from the second accommodating space 51 and face the vapor output channel 92. The supporting seat 40A may be provided with an open end, and the side wall of the supporting seat 40A located between the vaporization surface 11 and the open end and the vaporization surface 11 define a vaporization cavity. In addition, the air inlet path may be at least partially defined by an air inlet groove 47 on the supporting seat 40A, and the air inlet groove 47 may end at an air inlet 471. The air can sequentially flow through the second accommodating space 51 and the air inlet groove 47, and may be conveyed to the vaporization surface 11 of the liquid guide element 10 in the supporting seat 40A through the air inlet 471. The supporting seat 40A may be made into an integrated structure or formed by combination of separate structures.

Figure 14:
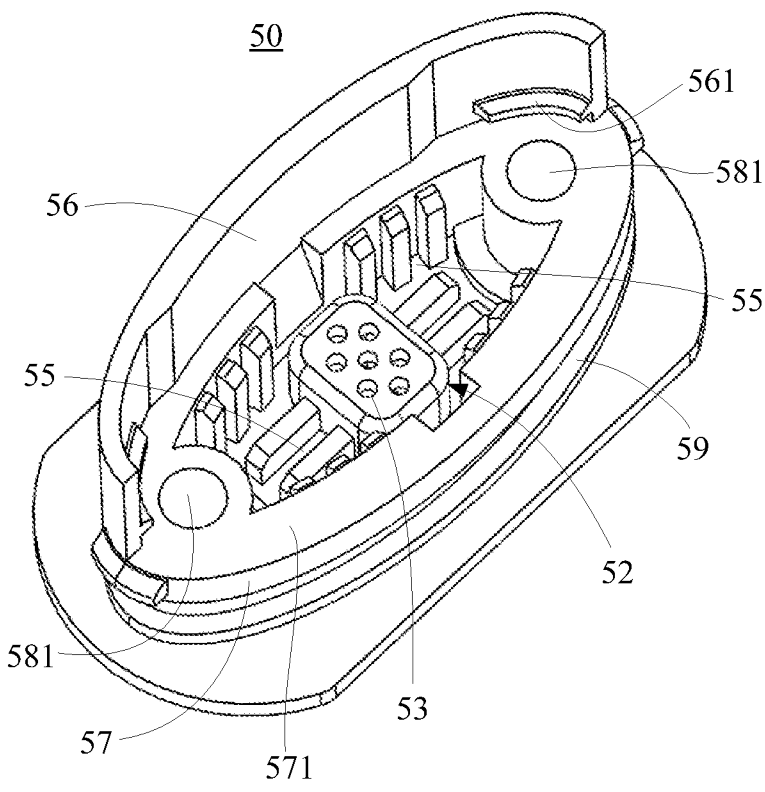
FIG. 14 is a three-dimensional schematic view of a second support of the vaporization core assembly shown in FIG. 8.

In some embodiments, with reference to FIG. 5, FIG. 8 and FIG. 14, the supporting seat 40A may also be provided with an air inlet tube 52, and the air inlet tube 52 is in communication with the second accommodating space 51 through a plurality of through holes 53. For example, the air inlet tube 52 may extend upwards from the bottom of the supporting seat 40A to the second accommodating space 51. The plurality of through holes 53 may be formed in an end wall 54 of the air inlet tube 52. In a depth direction of the second accommodating space 51, the end wall 54 is higher than the bottommost position of the second accommodating space 51 and lower than the separating plate 431. In this way, the part of the second accommodating space 51 in an outside direction of the air inlet tube 52 is actually formed into an anti-leakage container. Thus, even if the liquid leaks from the liquid accommodating space 91 or the liquid guide element 10 into the second accommodating space 51, the liquid will be accommodated by the second accommodating space 51 and will not leak to the outside of the vaporizer 100.

In addition, as shown in FIG. 8 and FIG. 14, at least one of a bottom surface and a side surface of the second accommodating space 51 may also be provided with a plurality of leaking liquid storage grooves 55. These leaking liquid storage grooves 55 may be recessed from the bottom surface and/or the side surface of the second accommodating space 51, or may be defined by a plurality of convex strips arranged on the bottom surface and/or the side surface of the second accommodating space 51. By forming these leaking liquid storage grooves 55, the liquid leaking into the second accommodating space 51 may be absorbed and stored by these leaking liquid storage grooves 55 through capillary action, thereby limiting the flow of the leaking liquid.

In some embodiments, with reference to FIG. 8, the supporting seat 40A may include a first support 40 and a second support 50 which are in matched connection. The separating plate 431, the air inlet 471 and the first accommodating space 45 are formed on the first support 40. The second accommodating space 51 is formed on the second support 50.

Figure 12:
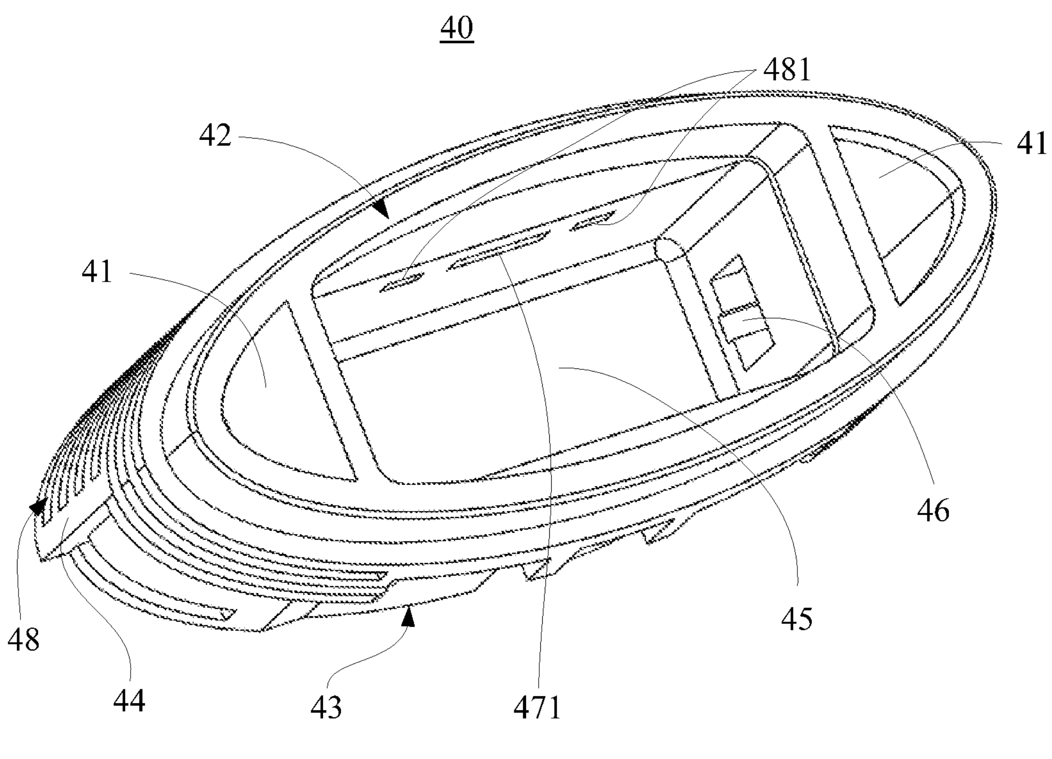
FIG. 12 is a three-dimensional schematic view of a first support of the vaporization core assembly shown in FIG. 8.
Figure 13:
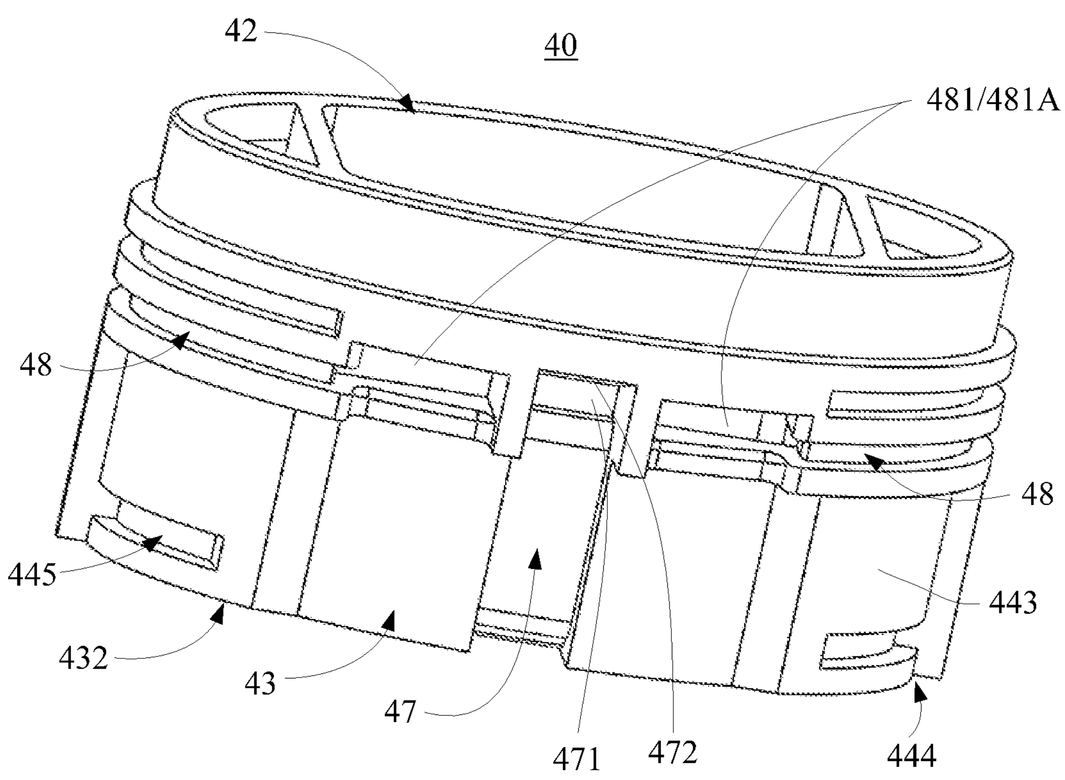
FIG. 13 is another three-dimensional schematic view of the first support shown in FIG. 12.

In some embodiments, with reference to FIG. 8, FIG. 12 and FIG. 13, the first support 40 may be provided with a second open end 42, a second closed end 43 opposite to the second open end 42, and a support side wall 44. The support side wall 44 and the second closed end 43 at least define the first accommodating space 45. During assembly, the liquid guide element 10 is configured to be placed from the second open end 42 into the first accommodating space 45 from top to bottom, so that the liquid guide element 10 is accommodated by the first accommodating space 45, and the vaporization surface 11 faces the second open end 42. Moreover, the support side wall 44 located between the vaporization surface 11 and the second open end 42 of the first accommodating space 45 and the vaporization surface 11 define a vaporization cavity. The vaporization cavity is a cavity where the heating element 20 on the vaporization surface 11 is located. When the heating element 20 works, the aerosol formed by heating and vaporizing the liquid is directly generated in the vaporization cavity and then outputted through the vapor output channel.

With reference to FIG. 8 and FIG. 12, after the liquid guide element 10 is placed in the first support 40, the second closed end 43 of the first support 40 can prevent the liquid absorbed by the liquid guide element 10 from leaking downwards, so that the anti-leakage effect is better.

In some embodiments, with reference to FIG. 12 and FIG. 13, the support side walls 44 are provided with the liquid inlet channel 41, and the liquid inlet channel 41 is configured to be in communication with the liquid inlet 34 formed in the first sealing member 30 so as to be in communication with the liquid absorbing surface 12 of the liquid guide element 10. For example, two opposite support side walls 44 of the first support 40 may be respectively provided with one liquid inlet channel 41. Further, the channel surface of each liquid inlet channel 41 may be provided with a guide groove 46 ending on an inner surface of the support side wall 44, and the guide groove 46 is concave relative to an adjacent channel surface. The guide groove 46 is configured to be aligned and communicated with the guide groove 35 of the first sealing member 30 installed in the first support 40, so that the liquid in the liquid accommodating space 91 may be guided into the first sealing member 30 through capillary action and then soaked and absorbed by the liquid guide element 10. The guide groove 46 may be formed in a channel surface in any direction of the liquid inlet channel 41, preferably in a bottom channel surface, so that the liquid first flows into the first sealing member 30 through the bottom under the action of gravity. In addition, with reference to FIG. 5, the liquid inlet channel 41 of the support side wall 44 may start from the second open end 42, and may face the second closed end 43 and extend to the vaporization surface 11 lower than the liquid guide element 10.

Correspondingly, with reference to FIG. 9, FIG. 12 and FIG. 13, the foregoing air inlet groove 47 may be arranged on the first support 40, for example, on an outer surface of the support side wall 44. The air inlet groove 47 may start from the second closed end 43 and end at the air inlet 471. On the support side wall 44, the air inlet 471 may be formed to penetrate from the outer surface of the support side wall 44 to the vaporization cavity. The vaporization surface 11 of the liquid guide element 10 accommodated in the first accommodating space 45 is further away from the second open end 42 than the air inlet 471. In other words, when taking the second open end 42 as a reference, the vaporization surface 11 is further away from the second open end 42 than the air inlet 471, so that the air inlet 471 is higher than the vaporization surface 11 of the liquid guide element 10 accommodated in the first accommodating space 45. Alternatively, the air inlet 471 may be located between the vaporization surface 11 and the second open end 42 and is closer to the vaporization surface 11, so that the air inlet 471 may be located above the vaporization surface 11 of the liquid guide element 10 accommodated in the first accommodating space 45 (including: the air inlet 471 is higher than the vaporization surface 11; and the lowest part of the air inlet 471 is flush with the vaporization surface 11). The air inlet groove 47 is configured to convey the air through the air inlet 471 to a space above the vaporization surface 11, that is, to the vaporization cavity. In this embodiment, by arranging the air inlet 471 to be higher than the vaporization surface 11 of the liquid guide element 10 accommodated in the first accommodating space 45, the liquid can be prevented from leaking from the vaporization surface 11 into the air inlet groove 47 through the air inlet 471.

In some embodiments, the air inlet 471 may be provided with an air guide structure, and the air guide structure is configured to guide the air from the air inlet path to the vaporization surface 11. For example, with reference to FIG. 9 and FIG. 13, the air guide structure may include an inclined plane 472 formed on the first support 40 of the supporting seat 40A and inclined relative to the vaporization surface 11. In a direction from the outer surface to the inner surface of the support side wall 44, the inclined plane 472 may gradually incline downwards to become closer to the vaporization surface 11. Thus, when the air is conveyed from the air inlet groove 47 to the air inlet 471, the air may be guided by the inclined plane 472 towards the vaporization surface 11.

In some embodiments, with reference to FIG. 7, FIG. 12 and FIG. 13, the outer surface of the support side wall 44 may be provided with a buffered liquid storage groove 48, and the buffered liquid storage groove 48 is in communication with the vaporization cavity. For example, the buffered liquid storage groove 48 may be in communication with the space above the vaporization surface 11 through an overflow port 481 formed in the support side wall 44, that is, in communication with the vaporization cavity.

In some embodiments, the first side of the first support 40 is provided with one first air inlet groove 47 and two first buffered liquid storage grooves 48. The first air inlet groove 47 is located between the two first buffered liquid storage grooves 48, and the air inlet 471 of the first air inlet groove 47 is located between the overflow ports 481 of the two first buffered liquid storage grooves 48. The first side of the first support 40 may be half of the side of the first support 40, and the half of the side is located on one side of a central axis surface passing through two opposite liquid inlet channels 41.

Further, a second side of the first support 40 may also be provided with one second air inlet groove 47 and two second buffered liquid storage grooves 48. The second air inlet groove 47 is located between the two second buffered liquid storage grooves 48, and the air inlet 471 of the second air inlet groove 47 is located between the overflow ports 481 of the two second buffered liquid storage grooves 48. In addition, one of the two first buffered liquid storage grooves 48 may be in communication with one of the two second buffered liquid storage grooves 48. The other one of the two first buffered liquid storage grooves 48 may be in communication with the other one of the two second buffered liquid storage grooves 48. The second side of the first support 40 may be the other half of the side of the first support 40, and the other half of the side is located on the other side of the central axis surface passing through two opposite liquid inlet channels 41.

Further, with reference to FIG. 5 and FIG. 12, the part of the first support 40, lower than the air inlet 471 or the vaporization surface 11, is actually formed into a container that is impermeable to the liquid. As a result, the liquid in the container can be prevented from leaking downwards, so the anti-leakage effect is better.

In some embodiments, with reference to FIG. 7, FIG. 12 and FIG. 13, the air inlet groove 47 and the buffered liquid storage groove 48 may be separated by a separating part 442 to prevent the liquid in the buffered liquid storage groove 48 from entering the air inlet groove 47. The buffered liquid storage groove 48 may be a capillary groove. By arranging the buffered liquid storage groove 48, the excessive liquid on the vaporization surface 11 may flow into the buffered liquid storage groove 48 through the overflow port 481, so that the buffered liquid storage groove 48 may absorb and store the overflowing liquid through capillary action to prevent the liquid from leaking to the other parts of the vaporizer 100. That is to say, the buffered liquid storage groove 48 can adsorb and maintain a condensate of the aerosol generated by the vaporizer 100 to prevent the condensate from seeping outwards. Particularly, when the air inlet groove 47 is located between two buffered liquid storage grooves 48, the gas enters the vaporization surface 11 of the liquid guide element 10 from the middle air inlet groove 47. When there is excessive condensate on the vaporization surface 11 of the liquid guide element 10, the condensate can be squeezed by the incoming gas towards the overflow ports 481 on both sides, and enters the buffered liquid storage grooves 48 from the overflow ports 481 on both sides, thereby effectively preventing the condensate from flowing from the air inlet groove 47 into the second support 50 and flowing outwards.

Further, a length of the buffered liquid storage groove 48 may be set to be greater than a circumference of the first support 40. For example, the buffered liquid storage groove 48 may adopt a circuitous and communicated slot structure, thereby forming a longer buffered liquid storage groove 48 on the outer surface of the first support 40. Particularly, the buffered liquid storage groove 48 may include a plurality of horizontal slots, and two adjacent slots may be communicated through a vertical slot. In addition, these vertical slots may be arranged to be not aligned in a vertical direction to allow the liquid to sequentially flow from the overflow ports 481 from the closer horizontal slot to the farther horizontal slot as much as possible. In addition, the overflow port 481 may be arranged to be higher than the vaporization surface 11 of the liquid guide element 10 accommodated in the first accommodating space 45.

In addition, with reference to FIG. 5, FIG. 12 and FIG. 13, the first support 40 may be in matched connection with the main housing 90, so that the vaporization surface 11 of the liquid guide element 10 accommodated in the first support 40 faces the vapor output channel 92, and the vaporization surface 11 is in airflow communication with the first end 921 serving as the lower end of the vapor output channel 92. During assembly, the first support 40 may be completely located in the main housing 90, and an outermost contour surface of the first support 40 is in basically matched contact with an inner side surface of the main housing 90. Thus, the inner side surface of the main housing 90 may be configured to seal lateral openings of the air inlet groove 47 and the buffered liquid storage groove 48 on the first side of the first support 40, and seal a lateral opening of the buffered liquid storage groove 48 on the second side of the first support 40. In addition, the lateral opening of the air inlet groove 47 on the second side of the first support 40 may be sealed through the second support 50.

In addition, in an embodiment including the first support 40 and the second support 50, the foregoing conductive element 60 may be arranged on the second support 50. For example, the conductive element 60 may be molded on the second support 50. More specifically, a majority of the first part 61 of the conductive element 60 may be molded in the second support 50. Moreover, after the first support 40 and the second support 50 are assembled, the second part 62 may be suspended in the first support 40. In addition, as shown in FIG. 13, the support side wall 44 of the first support 40 may be provided with a first matching surface 443. The first matching surface 443 may be configured to be in stop fit with the second support 50.

In some embodiments, with reference to FIG. 8 and FIG. 14, the second support 50 may include a main part 57 and a blocking wall 56, and the blocking wall 56 may be higher than the main part 57 and the second accommodating space 51 defined by the main part 57. The blocking wall 56 is arranged on one side of the second support 50. The blocking wall 56 is configured to be in matched connection with the first support 40. In addition, the separating plate 431 of the first support 40 may cover the second accommodating space 51. With reference to FIG. 13 and FIG. 14, a top surface 571 of the main part 57 and a bottom surface 432 of the second closed end 43 of the first support 40 are slidable relatively, so that the first matching surface 443 is in stop fit with the blocking wall 56. In this way, the first support 40 may be assembled to the second support 50 by transverse movement.

In some embodiments, with reference to FIG. 5, FIG. 8 and FIG. 14, the main part 57 of the second support 50 may be provided with an annular groove 572, and a sealing ring 59 is arranged in the annular groove 572. The sealing ring 59 may be made of a silicone sealant material. During assembly, the sealing ring 59 is configured to form a seal between the main part 57 and the main housing 90 to prevent the liquid from passing through. In addition, a magnetic attraction component 58 may be arranged in the second support 50. The magnetic attraction component 58 may be prepared from a ferromagnetic material such as stainless steel, so that after being received in the receiving cavity 270, the vaporizer 100 may be magnetically attracted to a magnetic attraction element arranged on the power supply assembly 200 to stably receive the vaporizer 100 in the receiving cavity 270. The magnetic attraction component 58 may be inserted into an installation hole 581 on the second support 50, and a lower end of the magnetic attraction component 58 is flush with a lower end of the second support 50.

In some embodiments, with reference to FIG. 13, the support side wall 44 of the first support 40 may have a vacant part 444, and the vacant part 444 forms the first matching surface 443. For example, in two opposite sides of the support side wall 44, a thickness of one side may become thinner relative to the other side so as to form the vacant part 444, and the vacant part 444 can be configured to accommodate the blocking wall 56 of the second support 50.

In addition, the first matching surfaces 443 may further include a positioning groove 445, and the blocking wall 56 may also be provided with a positioning block 561. The positioning block 561 is inserted into the positioning groove 445 to limit the first support 40 to move in a direction away from the second support 50. The positioning groove 445 may be a groove extending horizontally on the first matching surface 443. Correspondingly, the positioning block 561 is also horizontally arranged.

In some embodiments, with reference to FIG. 14, a cross section of the blocking wall 56 may be semi-annular. In other words, the cross section of the main part 57 may be annular, such as circular or elliptical, and the blocking wall 56 may be a part extending upwards from one side of the central axis surface of the main part 57. Thus, the semi-annular blocking wall 56 may form a semi-enclosed structure to cooperate with the support side wall 44 of the first support 40.

One of the foregoing air inlet grooves 47 may be defined between the first support 40 and the second support 50, for example, at least formed between the blocking wall 56 of the second support 50 and the first support 40. For another example, the air inlet groove 47 may be arranged on the outer surface of the support side wall 44 of the first support 40, and the position of the blocking wall 56 corresponding to the air inlet groove 47 may be a surface capable of covering the lateral opening of the air inlet groove 47. As a result, when the first support 40 and the second support 50 are in matched connection, the lateral opening of the air inlet groove 47 is covered by the blocking wall 56, so that the gas can only flow to the air inlet 471 of the air inlet groove 47 through a bottom opening of the air inlet groove 47, and will not flow outwards from a middle part of the air inlet groove 47.

In some embodiments, with reference to FIG. 8, FIG. 14 and FIG. 16, the conductive element 60 extends through the blocking wall 56, so that the blocking wall 56 plays a role in supporting the conductive element 60. Since the conductive element 60 may be made of sheet metal, in case of a longer length, the movement amplitude is larger due to insufficient strength. As a result, the first part 61 of the conductive element 60 may be fixed by the support of the blocking wall 56, thereby preventing excessive transverse movement of the second part 62 during assembly, and also ensuring that the first electrical contact 63 of the second part 62 and the conductive terminal 21 have sufficient pressure.

In another embodiment, the second support 50 may include a blocking wall (not shown) higher than the main part 57 and a reinforcing wall (not shown) higher than the main part 57. The conductive element 60 may extend through the reinforcing wall, so that the reinforcing wall plays a role in supporting the conductive element 60. At this time, the blocking wall may be a member separated from the reinforcing wall, which may only play a role in stop fit with the support side wall 44 of the first support 40. In other words, the blocking wall 56 shown in FIG. 14 may be divided into at least two parts separated from each other. One part serves as the reinforcing wall, and the other part serves as the blocking wall in this another embodiment.

In some embodiments, with reference to FIG. 12 and FIG. 13, the overflow port 481 formed on the side of the first support 40 with the vacant part 444 may also serve as a through hole 481A. The through hole 481A is arranged to be higher than the first matching surface 443, and is configured to insert the second part 62 of the conductive element 60. With reference to FIG. 16, the second part 62 of the conductive element 60 is bent relative to the first part 61 towards the through hole 481A. The second part 62 may extend into the first support 40 by the through hole 481A for conductive connection with the heating element 20 arranged on the liquid guide element 10. As described above, two through holes 481A and two conductive elements 60 may be provided. It is noted that the overflow port 481 and the through hole 481A herein may be the same through hole actually. This through hole may not only be configured for insertion of the second part 62 of the conductive element 60, but also serve as an overflow port for the excessive liquid on the vaporization surface 11 to flow outwards. In addition, in an assembly structure, the second part 62 of the conductive element 60 may only pass through the through hole 481A without contact with the through hole 481A, especially without contact with a lower surface of the through hole 481A. This can prevent the liquid from leaking outwards along the second part 62 by the through hole 481A.

Figure 15:
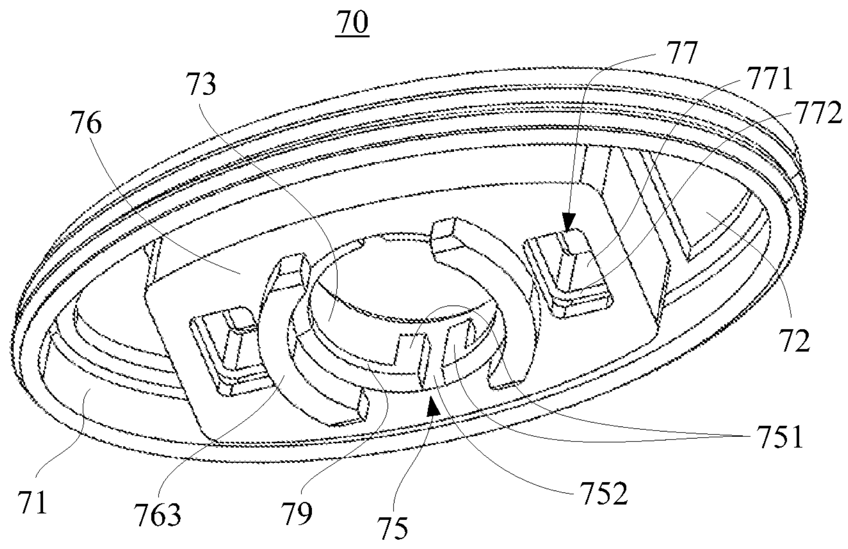
FIG. 15 is a three-dimensional schematic view of a second sealing member of the vaporization core assembly shown in FIG. 8.

In some embodiments, with reference to FIG. 8 and FIG. 15, the vaporization core assembly 10A of the vaporizer 100 may further include a second sealing member 70. The second sealing member 70 may include a base part 76 and a skirted part 71 extending from the periphery of the base part 76 to one side. The base part 76 may further be provided with a liquid guide hole 72 and a plug-in hole 73 as well as an installation hole 77 located between the liquid guide hole 72 and the plug-in hole 73. The second sealing member 70 may be made of a silicone sealant material. The second sealing member 70 is configured to sleeve the first support 40 of the supporting seat 40A, and the first support 40 of the supporting seat 40A is at least partially inserted into the main housing 90, so that the skirted part 71 of the second sealing member 70 is clamped between the first support 40 of the supporting seat 40A and the main housing 90 to form a seal, and the first end 921 of the vapor output channel 92 is configured to be inserted in the plug-in hole 73.

Further, the second sealing member 70 may be provided with a non-return valve 80A, and the non-return valve 80A is configured to be opened under the action of a pressure difference. As a result, in the assembled vaporizer 100, the air may be introduced into the liquid accommodating space 91 through the non-return valve 80A to avoid a larger negative pressure caused by the insufficient liquid in the liquid accommodating space 91, so that the liquid is smoothly outputted from the liquid accommodating space 91 to the liquid guide element 10. The non-return valve 80A may be a structure such as a duckbill valve which only allows the air to enter the liquid accommodating space 91 from the outside. In addition, since the vaporization surface 11 of the liquid guide element 10 may be arranged upwards, even if the liquid in the liquid accommodating space 91 leaks through the non-return valve 80A, the leaking liquid will also flow to the vaporization surface 11 and will be absorbed by the liquid guide element 10 or heated and vaporized on the vaporization surface 11.

Further, an airflow guide part 75 which protrudes from a hole wall and is configured to cooperate with the notch 922 at the tail end of the vapor output channel 92 may be arranged in the plug-in hole 73. For example, the airflow guide part 75 may be arranged at the end of the plug-in hole 73 away from the vapor output channel 92. The airflow guide part 75 may include two protrusions 751, and an airflow guide groove 752 is formed between the two protrusions 751. When the vapor output channel 92 is inserted into the plug-in hole 73, the airflow guide groove 752 extends for a certain distance from the outside of the vapor output channel 92 to the inside of the vapor output channel 92. As a result, when a user uses the vaporizer 100, if there is a condensate in the vapor output channel 92, the condensate can be guided downwards to the vaporization surface 11 by the airflow guide groove 752 to avoid the condensate from dripping onto the vaporization surface 11 after being condensed into large droplets, which may have an adverse impact on the vaporization quality.

In some embodiments, with reference to FIG. 8 and FIG. 15, the other side of the base part 76 away from the skirted part 71 may be provided with a valve plate 78, and the valve plate 78 correspond to the installation hole 77. A ventilation support 80 may be installed in the installation hole 77. The ventilation support 80 may be of a rigid structure and is provided with a vent hole 81 (referring to FIG. 5). The ventilation support 80 is installed in the installation hole 77, so that the valve plate 78 covers a port 82 of the vent hole 81. The valve plate 78 is configured to seal the port 82 or open the port 82 under the action of a pressure difference to play a role of a non-return valve. It is noted that the second sealing member 70 and the ventilation support 80 can form a vaporizer sealing assembly which is configured to form a seal between the first support 40 and the main housing 90. Furthermore, the ventilation support 80 can play a role in reinforcing the second sealing member 70 to avoid the deformation of the second sealing member 70 due to insufficient strength when the first end 921 of the vapor output channel 92 is inserted into the plug-in hole 73.

In some embodiments, with reference to FIG. 8, a first end 781 of the valve plate 78 is connected to the base part 76, and the other parts of the valve plate 78 are separated from the base part 76. In this way, the valve plate 78 may be more flexible, thereby facilitating the movement according to the action of a pressure difference.

Further, the base part 76 may be provided with a connecting block 761 and a concave part 762. The first end 781 of the valve plate 78 is connected to the connecting block 761. The concave part 762 is located on the side of the connecting block 761 away from the first end 781 of the valve plate 78. By arranging the concave part 762, the strength of the connecting block 761 connected to the first end 781 can be weakened, so that the valve plate 78 more easily moves under the action of a pressure difference and is not excessively constrained by the base part 76.

Further, with reference to FIG. 5 and FIG. 8, the vent hole 81 may be eccentrically arranged on the ventilation support 80, so that the vent hole 81 is closer to a second end 782 opposite the first end 781 of the valve plate 78. By this arrangement, an easily movable free end of the valve plate 78 can be matched with the vent hole 81.

In addition, the part where the ventilation support 80 is in contact with the valve plate 78 may be a lug boss 83, and the vent hole 81 penetrates through the lug boss 83. As shown in FIG. 5, the vent hole 81 may have a first section and a second section which are connected. The first section is close to the valve plate 78, and a cross-sectional size of the first section is less than a cross-sectional size of the second section.

In addition, with reference to FIG. 8, the ventilation support 80 may include a base part 84 and an annular flange 85 protruding from a side of the base part 84. The base part 84 may be a cylinder extending uniformly from bottom to top, and the cross section of the base part 84 may be square, circular or elliptical, or may be in a similar shape, especially a rectangular shape with four arc chamfers. Correspondingly, with reference to FIG. 14, the installation hole 77 may include a first part 771 for accommodating the base part 84 and a second part 772 for accommodating the annular flange 85. The annular flange 85 is in stop fit with the second part 772, which can prevent the ventilation support 80 from falling off from the second sealing member 70. Furthermore, a matching surface of the annular flange 85 and the second part 772 also forms a tortuous path in an up and down direction, which can better prevent the liquid from leaking.

In addition, two installation holes 77 may be provided, the plug-in hole 73 may be arranged in a center position of the base part 76, and one installation hole 77 is arranged between each liquid guide hole 72 and the plug-in hole 73.

Further, as shown in FIG. 15, the two installation holes 77 may be symmetrically arranged relative to the plug-in hole 73. In addition, as shown in FIG. 8, the two connecting blocks 761, the two concave parts 762 and the two valve plates 78 may be rotationally and symmetrically arranged with respect to the plug-in hole 73.

In some embodiments, as shown in FIG. 15, a thickness of the base part 76 where the liquid guide hole 72 is located may be less than a thickness of the base part 76 where the installation hole 77 is located. In addition, an upper surface of the base part 76 may be located in a plane.

In addition, the end of the plug-in hole 73 away from the valve plate 78 may also be provided with a stop part 79, and the stop part 79 protrudes inwards from the plug-in hole 73 to abut against the vapor output channel 92 in the main housing 90. An inner surface of the stop part 79 may be aligned with an inner surface of the vapor output channel 92. That is to say, they may be located in a cylindrical surface of a same, for example, cylinder. In addition, the two protrusions 751 of the airflow guide part 75 may extend upwards from a tail end of the stop part 79. Inner surfaces of the two protrusions 751 may also be aligned with the inner surface of the vapor output channel 92. That is to say, they may be located in a cylindrical surface of a same, for example, cylinder.

In some embodiments, as shown in FIG. 15, the other side of the base part 76 away from the valve plate 78 may also be provided with a convex ridge part 763, and the convex ridge part 763 is located between the plug-in hole 73 and the installation hole 77. For example, the convex ridge part 763 may be of an arc structure arranged adjacent to the plug-in hole 73. Two convex ridge parts 763 may be provided and may be arranged oppositely with respect to the plug-in hole 73. When the second sealing member 70 sleeves the first support 40, two tail ends of each convex ridge part 763 abut against an inner surface of the first support 40. In this way, a step is formed between the convex ridge part 763 and a lower surface of the base part 76, and the step can prevent the formation of a vortex during suction of the vaporizer 100. In addition, since an accommodating space is formed between the step and the first support 40, which can be configured to accommodate a condensate accumulated in the vaporization cavity when the vaporizer 100 is inverted, so as to prevent the condensate from flowing out of the vapor output channel 92 when the vaporizer 100 is inverted.

In some embodiments, with reference to FIG. 8 and FIG. 15, the first support 40 of the supporting seat 40A defines that a side wall of the first accommodating space 45 may be provided with a step part 441, and the step part 441 is configured to support the part of the second sealing member 70 inserted into the first accommodating space 45. As a result, when the first end 921 of the vapor output channel 92 is inserted into the plug-in hole 73, the second sealing member 70 can also be supported by the step part 441 to avoid the deformation of the second sealing member 70 due to the loss of support.

Figure 17:
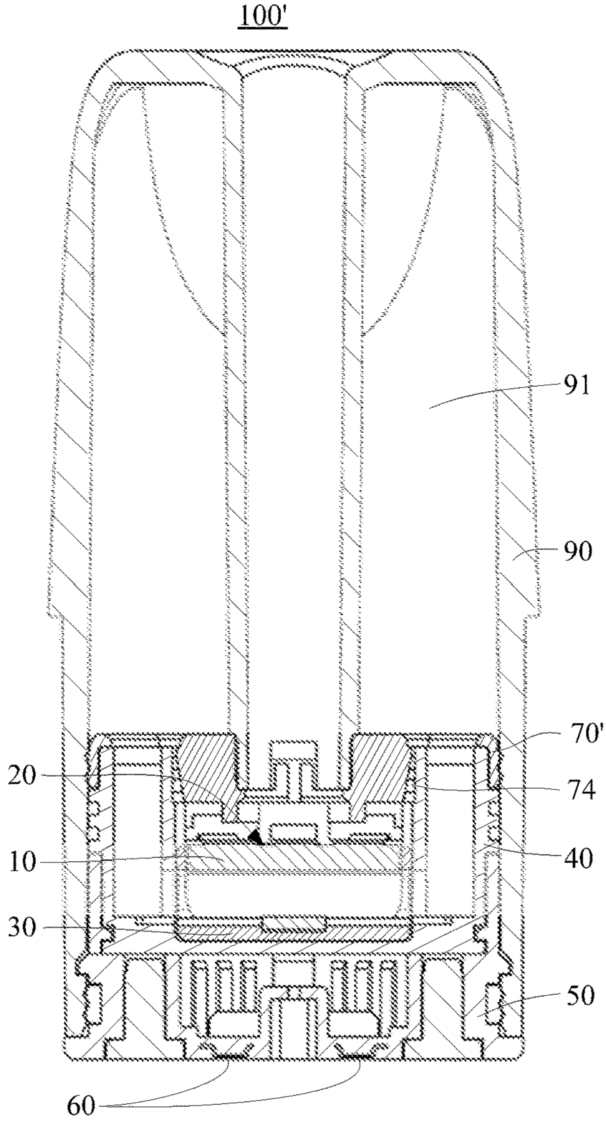
FIG. 17 is a schematic cross-sectional view of a vaporizer provided in another embodiment of this application.
Figure 18:
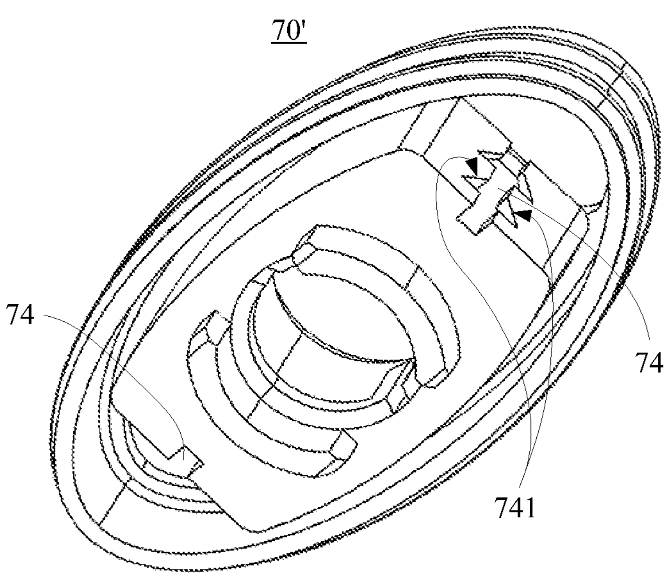
FIG. 18 is a three-dimensional schematic view of a second sealing member of the vaporizer shown in FIG. 17.

FIG. 17 shows a schematic cross-sectional view of a vaporizer 100' provided in another embodiment of this application. In an embodiment shown in FIG. 17, the vaporizer 100' is different from the vaporizer 100 shown in FIG. 2 to FIG. 16 only in terms of the second sealing member 70, and other structures may be completely identical. For example, the vaporizer 100' may include the same liquid guide element 10, heating element 20, first sealing member 30, first support 40, second support 50, conductive elements 60 and main housing 90. However, a second sealing member 70' in the vaporizer 100' may be different from the second sealing member 70 in the vaporizer 100 shown in FIG. 2 to FIG. 16. Specifically, as shown in FIG. 18, the second sealing member 70' and the second sealing member 70 may have different ventilation modes. The second sealing member 70' may be provided with a ventilation groove 74. The ventilation groove 74 is configured to be in communication with the atmosphere and the liquid accommodating space 91 in the main housing 90, so as to convey the air into the liquid accommodating space 91 under the action of a pressure difference. When the second sealing member 70' sleeves the first support 40, an opening of the ventilation groove 74 facing the first support 40 is covered by the inner surface of the first support 40, so as to form a gas channel extending from a bottom side to a top side of the second sealing member 70'. The ventilation groove 74 may be a capillary groove which may be a groove extending uniformly up and down on one side of the second sealing member 70'. Further, two opposite groove surfaces of the groove extending uniformly up and down may also be provided with a plurality of square or triangular concave parts 741. Due to the capillary action, the liquid from the liquid accommodating space 91 may be maintained in the ventilation groove 74. Only when a negative pressure of the liquid accommodating space 91 reaches a certain degree, the external air may enter the liquid accommodating space 91 under the action of a pressure difference.

Figure 19:
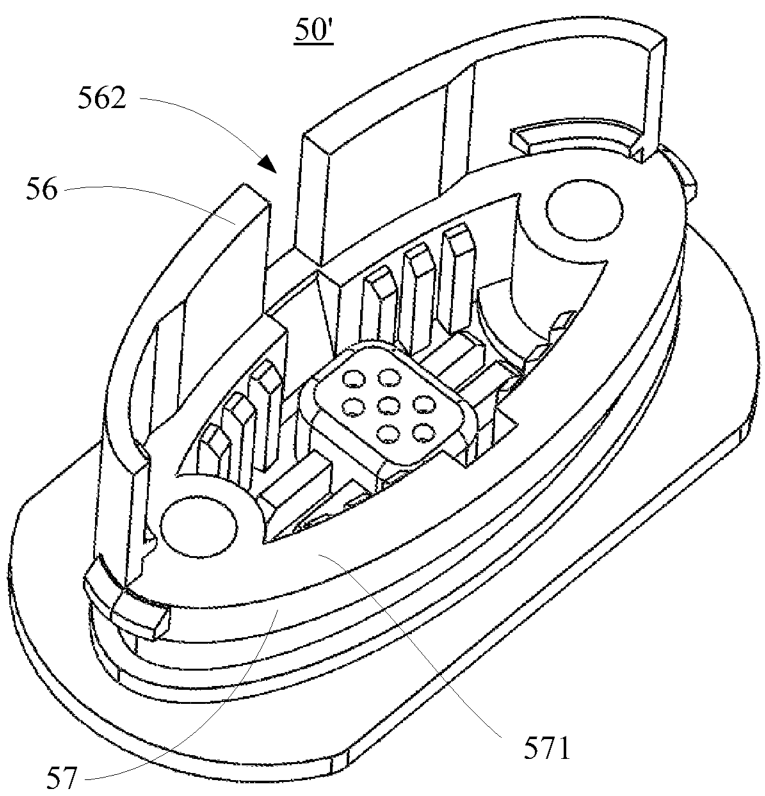
FIG. 19 is a three-dimensional schematic view of a second support provided in another embodiment of this application.

FIG. 19 shows a three-dimensional schematic view of a second support 50' provided in another embodiment of this application. In an embodiment shown in FIG. 19, the second support 50' is different from the second support 50 shown in FIG. 2 to FIG. 18 only in terms of the blocking wall 56, and other structures may be completely identical; and the second support 50' may also be applied to the vaporizer 100 shown in FIG. 2 to FIG. 18. Specifically, as shown in FIG. 19, the part of the blocking wall 56, corresponding to the second air inlet groove 47 on the second side of the first support 40 shown in FIG. 13, may be provided with a groove 562. For example, the groove 562 may penetrate through a thickness direction of the blocking wall 56, and may be formed in a top surface 571 of a main part 57 of the second support 50'. As a result, when the second support 50' is applied to the vaporizer 100 shown in FIG. 2 to FIG. 18, the first air inlet groove 47 formed in the first side of the first support 40 forms a first air inlet channel, and the first air inlet channel is in communication with the vaporization surface 11 of the liquid guide element 10 accommodated in the first support 40. The groove 562 and the second air inlet groove 47 form a second air inlet channel together, and the second air inlet channel is also in communication with the vaporization surface 11. The first air inlet channel and the second air inlet channel may have a same channel size. For example, the first air inlet channel and the second air inlet channel may have a roughly same shape, so that the air inflow on both sides of the first support 40 can remain consistent to obtain a better vaporization effect. Alternatively, it may simply ensure that the minimum cross-sectional areas of the first air inlet channel and the second air inlet channel are the same, which can also ensure that the air inflow on both sides of the first support 40 remains consistent.

Figure 20:
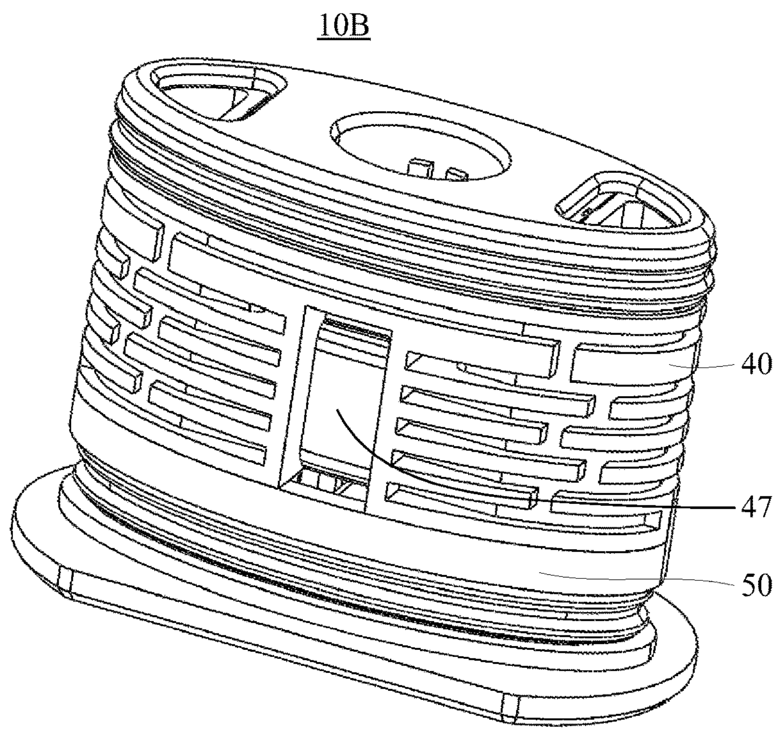
FIG. 20 is a three-dimensional schematic view of a vaporization core assembly provided in another embodiment of this application.
Figure 21:
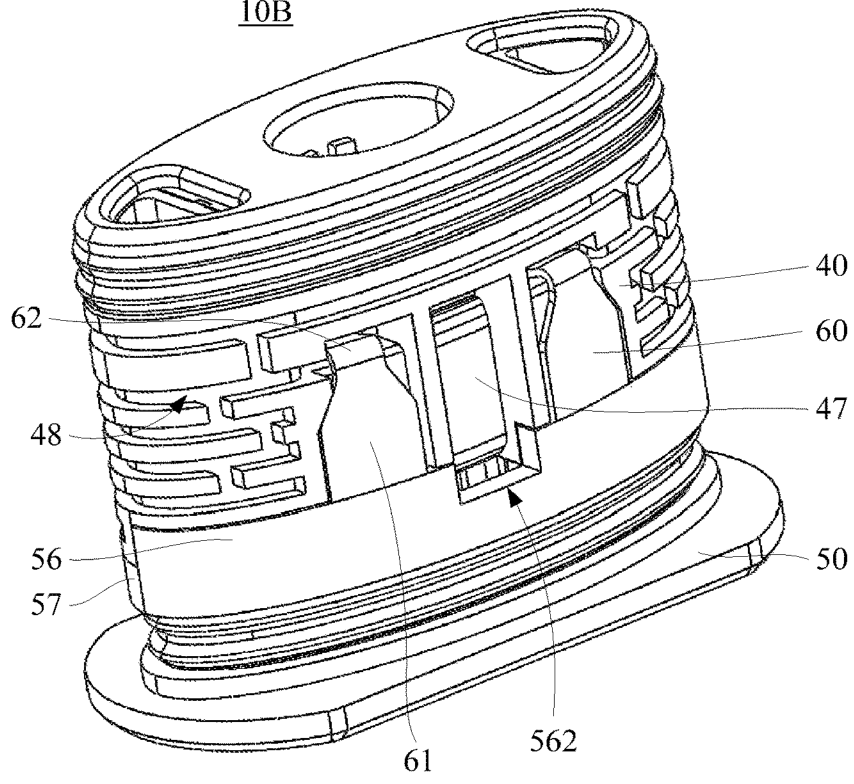
FIG. 21 is another three-dimensional schematic view of the vaporization core assembly shown in FIG. 20.

FIG. 20 and FIG. 21 show three-dimensional schematic views of a vaporization core assembly 10B provided in another embodiment of this application. In embodiments shown in FIG. 20 and FIG. 21, the vaporization core assembly 10B is different from the vaporization core assembly 10A shown in FIG. 2 to FIG. 18 only in terms of the first support 40, the second support 50 and the conductive elements 60, and other structures may be completely identical. Specifically, as shown in FIG. 20, a first side of the first support 40 is provided with a first air inlet groove 47. The first air inlet groove 47 is configured to form a first air inlet channel, and the first air inlet channel is in communication with the vaporization surface 11 of the liquid guide element 10 accommodated in the first support 40. As shown in FIG. 21, a second side of the first support 40 is provided with a second air inlet groove 47. The part of the blocking wall 56 of the second support 50, corresponding to the second air inlet groove 47, is provided with a groove 562. The groove 562 and the second air inlet groove 47 form a second air inlet channel together. The second air inlet channel is also in communication with the vaporization surface 11. Similarly, the first air inlet channel and the second air inlet channel may have a same channel size, so that the air inflow on both sides of the first support 40 may remain consistent to obtain a better vaporization effect. Compared with the second support 50' shown in FIG. 19, the blocking wall 56 of the second support 50 shown in FIG. 21 is lower. Correspondingly, the side wall part defining the buffered liquid storage groove 48 on the second side of the first support 40 may be higher to form a complementary structure with the blocking wall 56. In addition, since the blocking wall 56 shown in FIG. 21 is lower, the part in a vertical direction of the first part 61 of the conductive element 60 on the second support 50 may be set to be wider than the second part 62, and then, the first part 61 may also play a certain supporting role to prevent excessive transverse movement of the second part 62 during assembly. It is noted that it is not necessary to set all the parts in the vertical direction of the first part 61 of the conductive element 60 to be wider, as long as a part extending from the blocking wall 56 and another part adjacent to this part and embedded in the blocking wall 56 are wider. The above introduces the electronic vaporization device 300 and various components of the vaporizer 100 thereof of this application. When the electronic vaporization device 300 needs to be used for suction, a power switch of the power supply assembly 200 may be turned on first, so that the power supply assembly 200 can supply power to the vaporizer 100. Then, when a user sucks air through a suction nozzle where the suction port 94 of the vaporizer 100 is located, the controller 220 of the electronic vaporization device 300 can start the vaporizer 100 to work according to the suction action, so as to finally generate an aerosol for the user to suck. The liquid from the liquid accommodating space 91 is heated and vaporized by the heating element 20 to form the aerosol, and the external air may sequentially flow through the air inlet tube 52, the second accommodating space 51 and the air inlet groove 47 and is conveyed to the space above the vaporization surface 11 of the liquid guide element 10 in the first support 40 through the air inlet 471, so that the formed aerosol is carried out of the vapor output channel 92.

Finally, it should be noted that: the foregoing embodiments are merely used for describing the technical solutions of this application, but are not intended to limit this application. Under the ideas of this application, the technical features in the foregoing embodiments or different embodiments may also be combined, the steps may be performed in any order, many other changes in different aspects of this application also exist as described above, and these changes are not provided in detail for simplicity. Although this application is described in detail with reference to the foregoing embodiments, it should be understood by a person skilled in the art that, modifications may still be made to the technical solutions described in the foregoing embodiments, or equivalent replacements may be made to the part of the technical features; and these modifications or replacements will not cause the essence of corresponding technical solutions to depart from the scope of the technical solutions in the embodiments of this application.

What is claimed is:

1. A vaporizer, configured to vaporize a liquid substrate to generate an aerosol, wherein the vaporizer comprises:

a main housing, defining a vapor output channel located in the main housing;

a liquid guide element, comprising a vaporization surface and a liquid absorbing surface;

a heating element, arranged on the vaporization surface and configured to heat at least a part of the liquid substrate absorbed by the liquid guide element to generate an aerosol; and a supporting seat, defining a first accommodating space and a second accommodating space separated by a separating plate, the first accommodating space accommodating the liquid guide element, and the supporting seat being in matched connection with the main housing, so that the vaporization surface of the liquid guide element faces the vapor output channel;

wherein an air inlet path is formed between the first accommodating space and the second accommodating space, and the air inlet path is configured to guide and convey the air in the second accommodating space to the vicinity of the vaporization surface located in the first accommodating space; and wherein the air inlet path is at least partially defined by an air inlet groove on the supporting seat, and the air inlet groove ends at an air inlet higher than the vaporization surface.

2. The vaporizer according to claim 1, wherein:

the supporting seat is provided with an open end, a side wall of the supporting seat is located between the vaporization surface and the open end, and the side wall and the vaporization surface define a vaporization cavity.

3. The vaporizer according to claim 1, wherein the air inlet is provided with an air guide structure, and the air guide structure is configured to guide the air from the air inlet path to the vaporization surface.

4. The vaporizer according to claim 3, wherein the air guide structure comprises an inclined plane formed on the supporting seat and inclined relative to the vaporization surface.

5. The vaporizer according to claim 1, wherein:

the side wall of the supporting seat is provided with a liquid inlet channel, and the liquid inlet channel is in communication with the liquid absorbing surface of the liquid guide element.

6. The vaporizer according to claim 1, wherein:

the supporting seat is further provided with an air inlet tube, and the air inlet tube is in communication with the second accommodating space through a plurality of through holes.

7. The vaporizer according to claim 6, wherein:

the plurality of through holes are formed in an end wall of the air inlet tube; and in a depth direction of the second accommodating space, the end wall is higher than the bottommost position of the second accommodating space and lower than the separating plate.

8. The vaporizer according to claim 1, wherein:

at least one of a bottom surface and a side surface of the second accommodating space is provided with a plurality of leaking liquid storage grooves 55.

9. The vaporizer according to claim 1, wherein:

the supporting seat comprises a first support and a second support which are in matched connection, the separating plate, an air inlet and the first accommodating space are formed on the first support, and the second accommodating space is formed on the second support.

10. The vaporizer according to claim 9, wherein:

the second support further comprises a blocking wall, and the blocking wall is arranged on one side of the second support;

the blocking wall is in matched connection with the first support; and the air inlet path is at least formed between the blocking wall and the first support.

11. The vaporizer according to claim 1, wherein:

the liquid guide element comprises a first wall part where the vaporization surface is located and two second wall parts extending from both sides of the first wall part away from the vaporization surface respectively, and the surface of the first wall part located between the two second wall parts forms at least a part of the liquid absorbing surface.

12. The vaporizer according to claim 1, wherein:

the vaporizer further comprises a first sealing member; and the first sealing member is located between the liquid guide element and a support side wall of the supporting seat to seal and isolate the vaporization surface and the liquid absorbing surface.

13. The vaporizer according to claim 1, wherein:

the supporting seat is further provided with a conductive element, and the conductive element abuts against the heating element to conduct electricity, and at least partially extends or is exposed outside the supporting seat to form a first electrical contact for supplying power to the heating element.

14. The vaporizer according to claim 1, wherein:

the vaporizer further comprises a second sealing member, and the second sealing member has a skirted part arranged in a circumferential direction and is provided with a liquid guide hole and a plug-in hole; and the second sealing member sleeves the supporting seat, and the supporting seat is at least partially inserted into the main housing, so that the skirted part of the second sealing member is clamped between the supporting seat and the main housing to form a seal, and a first end of the vapor output channel is inserted in the plug-in hole.

15. The vaporizer according to claim 14, wherein:

the second sealing member is provided with a ventilation groove, and the ventilation groove are in communication with the atmosphere and the liquid accommodating space, so as to convey the air into the liquid accommodating space under the action of a pressure difference;

or the second sealing member is provided with a non-return valve, and the non-return valve is configured to be opened under the action of a pressure difference to convey the air into the liquid accommodating space.

16. The vaporizer according to claim 1, wherein:

the supporting seat defines that a side wall of the first accommodating space is provided with a step part, and the step part supports the part of the second sealing member inserted into the first accommodating space.

17. An electronic vaporization device, comprising a vaporizer configured to vaporize a liquid substrate to generate an aerosol, and a power supply assembly configured to supply power to the vaporizer, wherein the vaporizer comprises the vaporizer according to claim 1.

* * * * *